United States Patent
Beck

(10) Patent No.: US 9,047,999 B2
(45) Date of Patent: Jun. 2, 2015

(54) THREE-DIMENSIONAL FOCUSED ANTI-SCATTER GRID AND METHOD FOR MANUFACTURING THEREOF

(75) Inventor: Thomas J. Beck, Baltimore, MD (US)

(73) Assignee: Turtle Bay Partners, LLC, Littlestown, PA (US)

( * ) Notice: Subject to any disclaimer, the term of this patent is extended or adjusted under 35 U.S.C. 154(b) by 687 days.

(21) Appl. No.: 13/271,018

(22) Filed: Oct. 11, 2011

(65) Prior Publication Data

US 2012/0087477 A1    Apr. 12, 2012

Related U.S. Application Data

(60) Provisional application No. 61/391,536, filed on Oct. 8, 2010.

(51) Int. Cl.
*G21K 1/02* (2006.01)
*A61B 6/00* (2006.01)

(52) U.S. Cl.
CPC .......... *G21K 1/025* (2013.01); *G01N 2223/316* (2013.01); *Y10T 29/49826* (2015.01); *A61B 6/508* (2013.01)

(58) Field of Classification Search
CPC .......... G21K 1/02; G21K 1/025; G21K 1/10; G01N 2223/316
USPC ......................................... 378/149, 154, 186
See application file for complete search history.

(56) References Cited

U.S. PATENT DOCUMENTS

| | | | | |
|---|---|---|---|---|
| 1,476,048 A | * | 12/1923 | Bucky | 378/154 |
| 2,133,385 A | * | 10/1938 | Freeman | 378/154 |
| 3,143,652 A | * | 8/1964 | Bigelow | 378/147 |
| 3,919,559 A | * | 11/1975 | Stevens | 378/154 |
| 4,115,695 A | | 9/1978 | Kelman | |
| 4,340,818 A | * | 7/1982 | Barnes | 378/155 |
| 4,419,585 A | * | 12/1983 | Strauss et al. | 250/505.1 |
| 4,970,398 A | | 11/1990 | Scheid | |
| 5,099,134 A | * | 3/1992 | Hase et al. | 250/505.1 |
| 5,487,098 A | | 1/1996 | Dobbs et al. | |
| 5,721,761 A | * | 2/1998 | Ferlic et al. | 378/154 |
| 5,949,850 A | * | 9/1999 | Tang | 378/154 |
| 6,363,136 B1 | * | 3/2002 | Flisikowski et al. | 378/154 |
| 6,470,072 B1 | * | 10/2002 | Johnson | 378/154 |
| 6,594,878 B2 | * | 7/2003 | Kohda | 29/417 |
| 6,707,884 B1 | * | 3/2004 | Ogawa | 378/154 |
| 6,801,600 B2 | * | 10/2004 | Kohda | 378/154 |
| 6,987,836 B2 | * | 1/2006 | Tang et al. | 378/154 |
| 7,072,446 B2 | | 7/2006 | Dobbs et al. | |
| 7,318,524 B2 | | 1/2008 | Compton et al. | |
| 7,564,940 B2 | * | 7/2009 | Mattson et al. | 378/19 |
| 7,785,098 B1 | * | 8/2010 | Appleby et al. | 425/470 |
| 8,418,348 B2 | * | 4/2013 | Tonami | 29/592.1 |
| 8,712,715 B2 | * | 4/2014 | Tonami | 702/104 |
| 2004/0008810 A1 | | 1/2004 | Nelson et al. | |

(Continued)

*Primary Examiner* — Thomas R Artman
(74) *Attorney, Agent, or Firm* — Barry G. Magidoff; Paul J. Sutton

(57) ABSTRACT

A device for, and method of manufacture of, a focused anti-scatter grid for improving the image contrast of x-ray images produced in medical, veterinary or industrial applications. The grid comprising a series of modular units so juxtaposed with each other as to form a series of focused channels for the passage of the focused imaging x-rays. The modules comprise a series of focusing ribbons of a heavy metal or a series of mating solid arcuate forms, formed of a polymer and having on at least one side surface a layer of heavy metal.

9 Claims, 23 Drawing Sheets

(56) References Cited

U.S. PATENT DOCUMENTS

| | | |
|---|---|---|
| 2007/0259817 A1 | 11/2007 | Brooks et al. |
| 2009/0238324 A1* | 9/2009 | Oikawa .............................. 378/7 |
| 2009/0323899 A1 | 12/2009 | Dorscheid et al. |
| 2012/0087477 A1* | 4/2012 | Beck .............................. 378/154 |
| 2013/0272505 A1* | 10/2013 | Beck .............................. 378/154 |
| 2013/0322603 A1* | 12/2013 | Kurochi et al. ................ 378/147 |

* cited by examiner

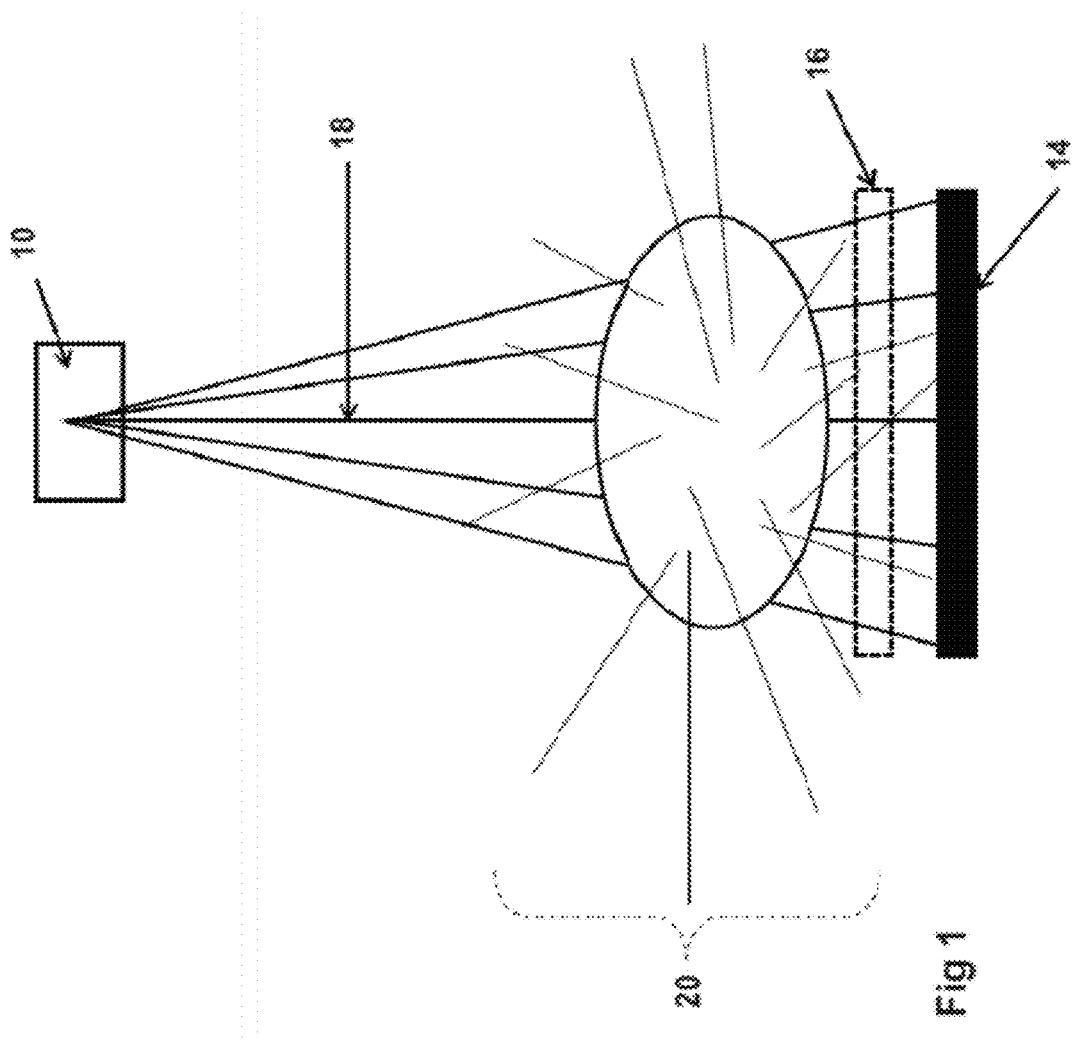

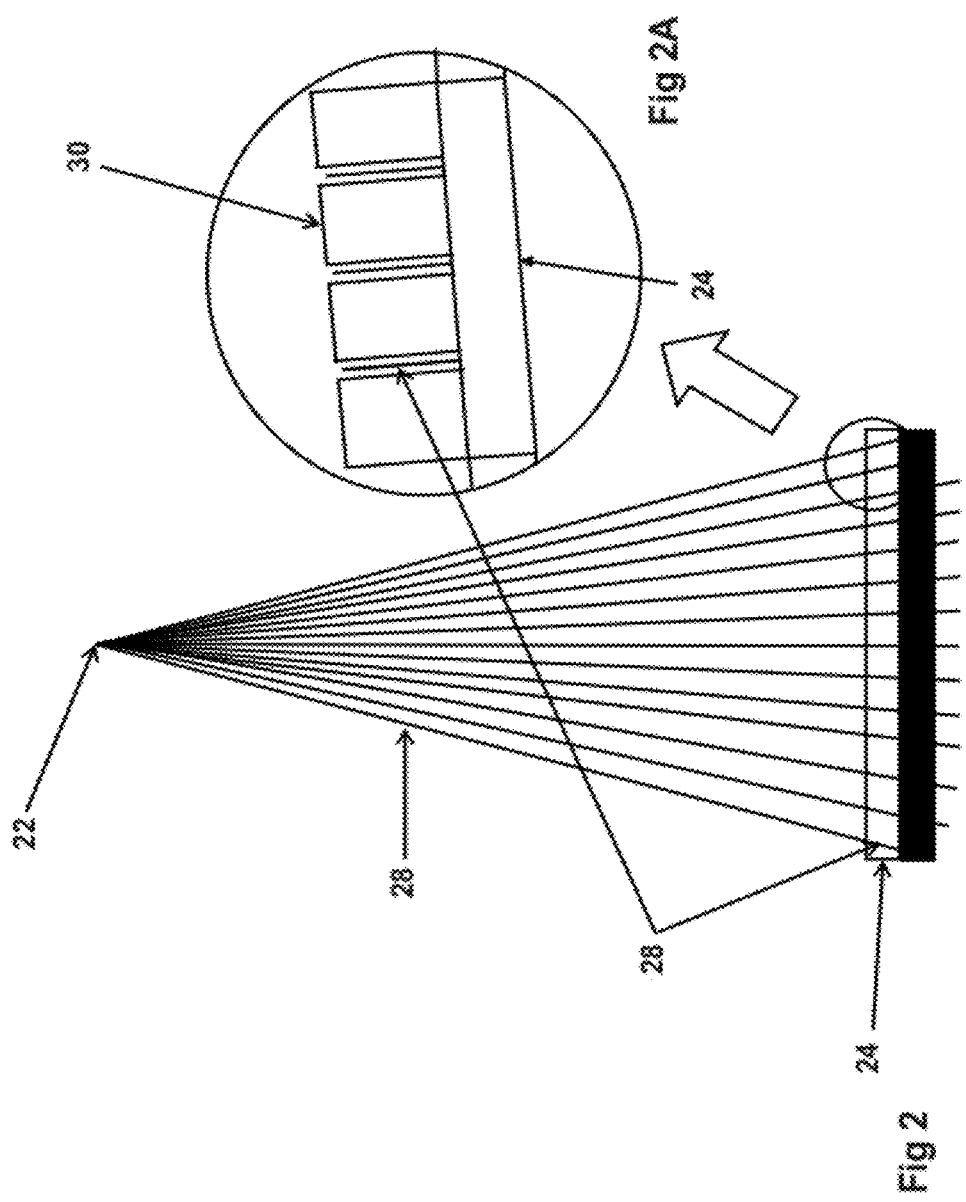

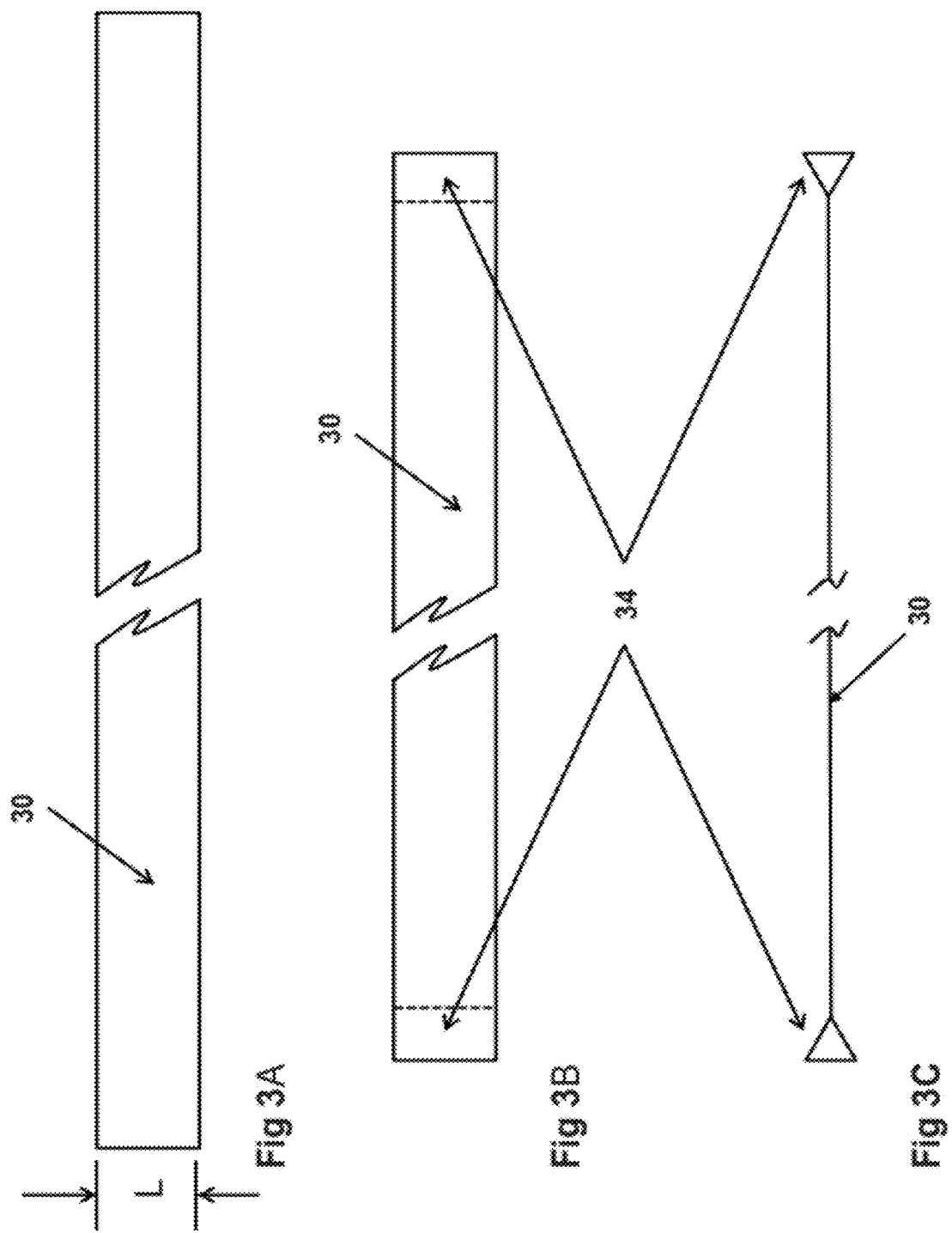

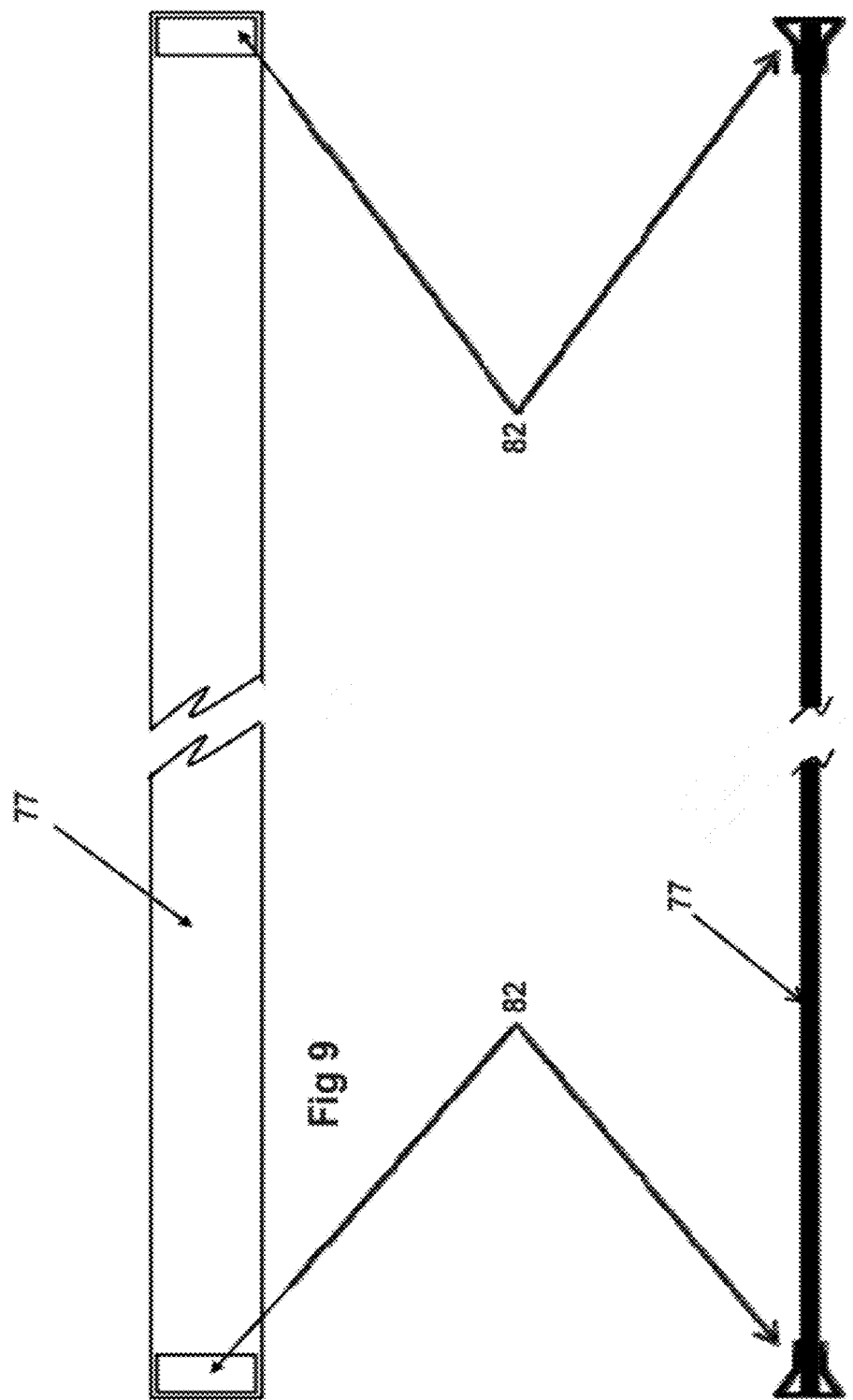

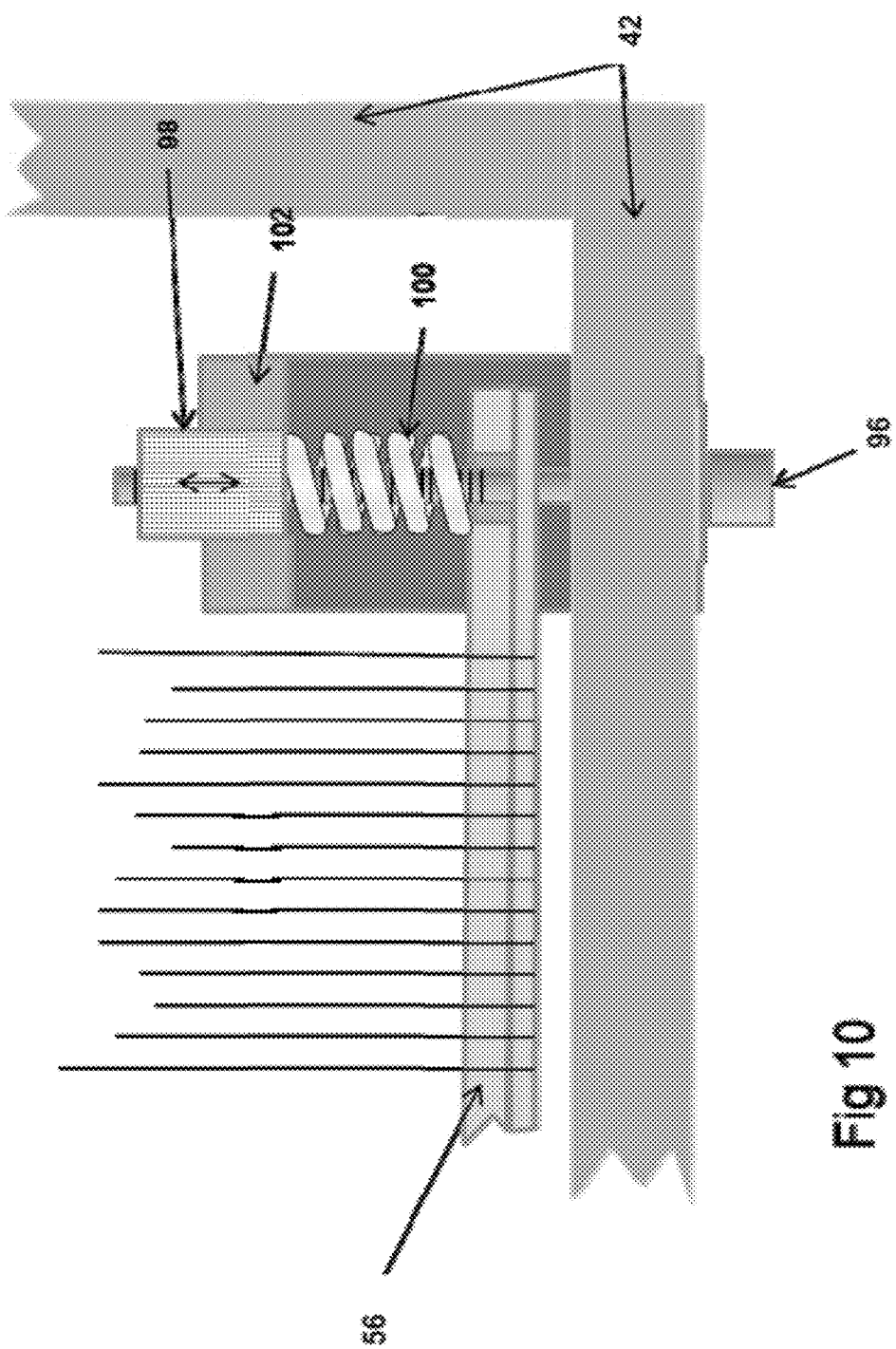

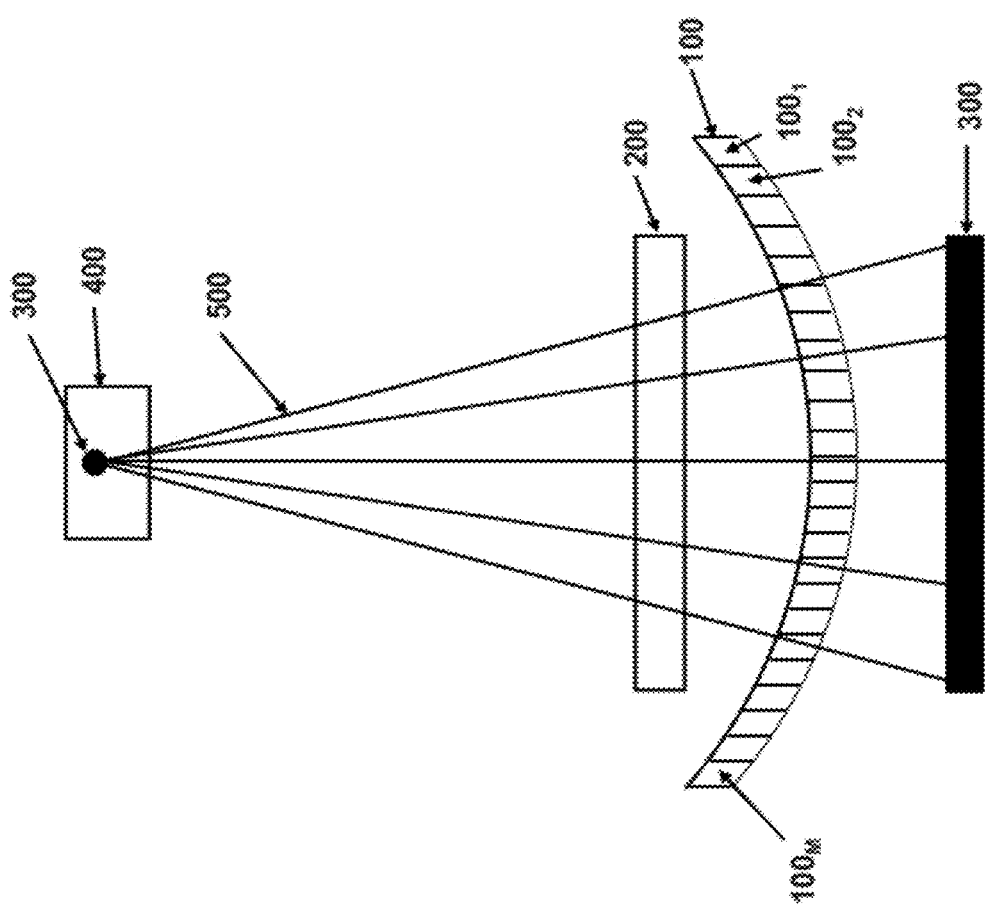

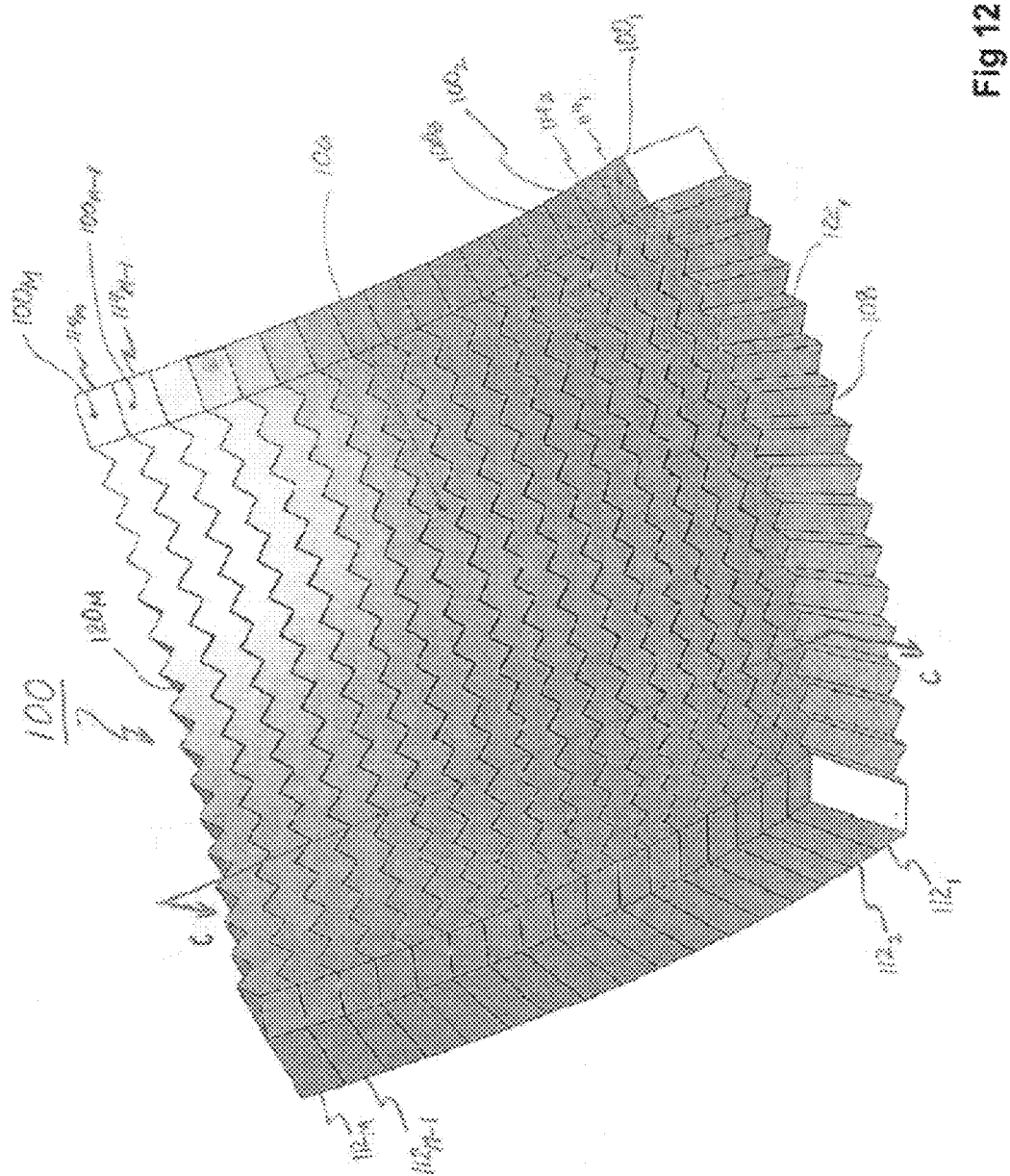

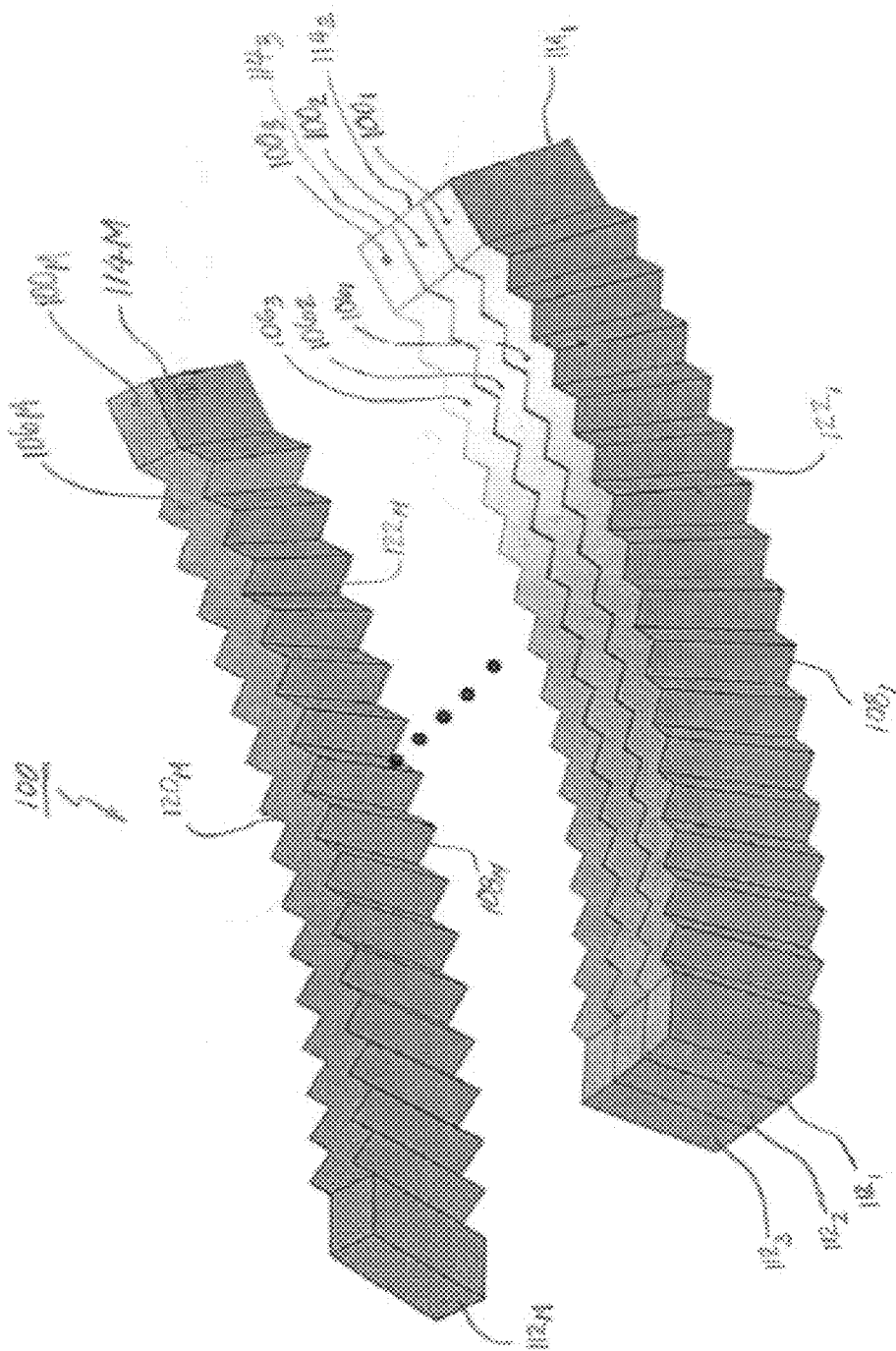

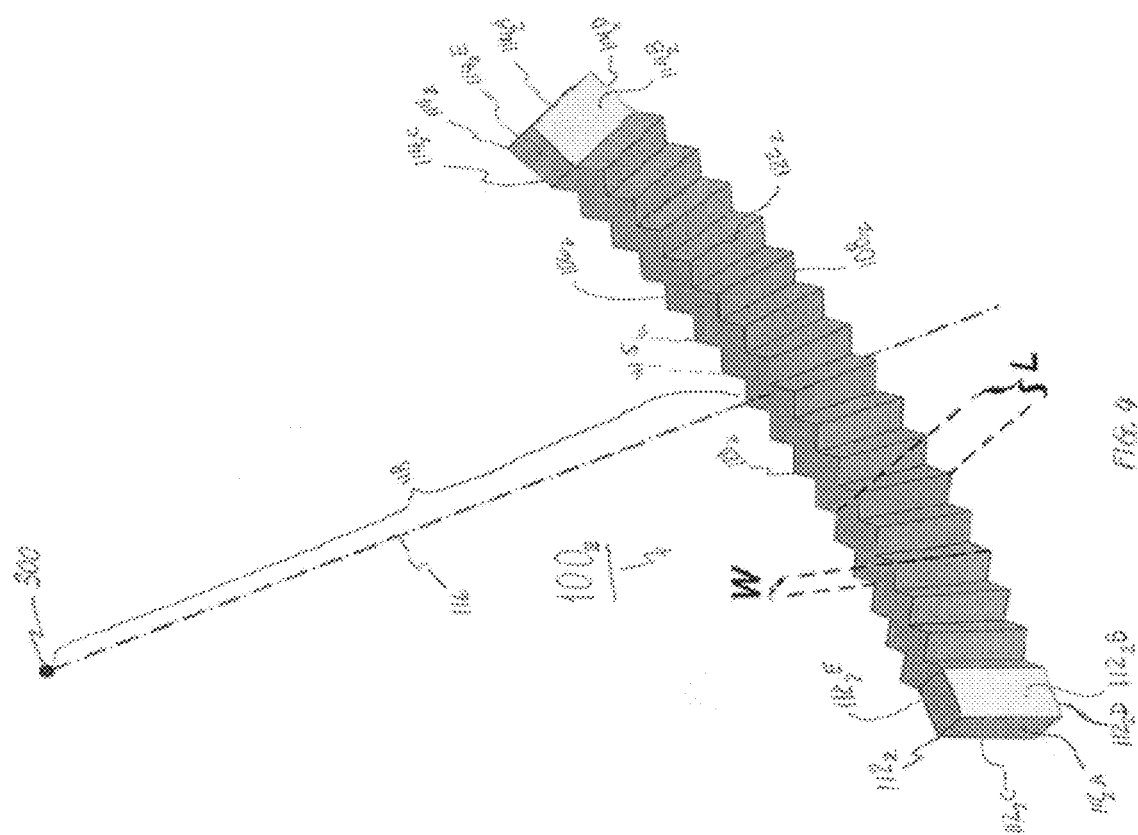

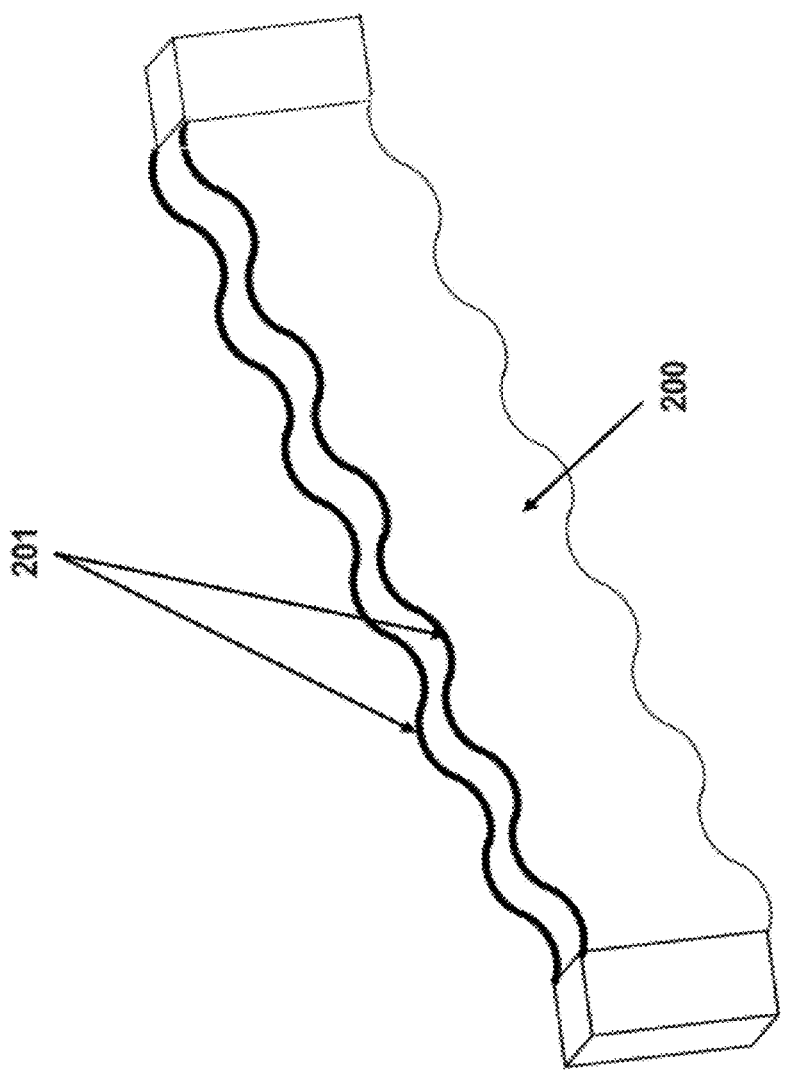

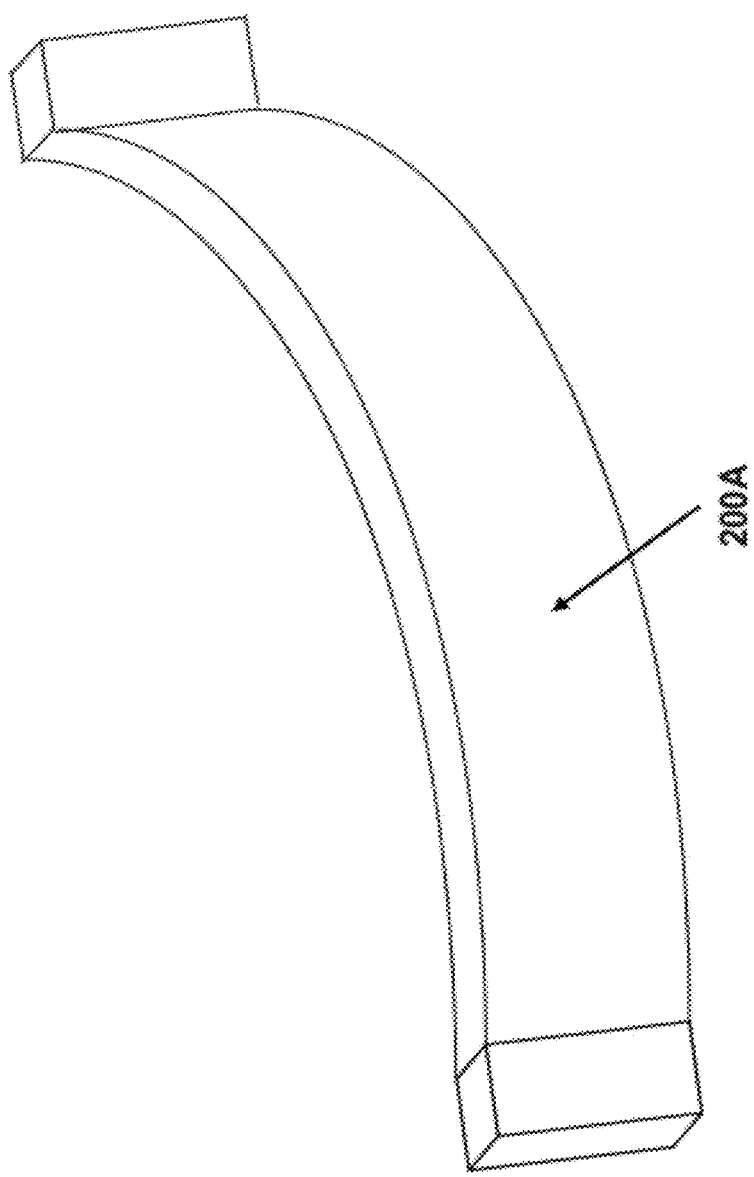

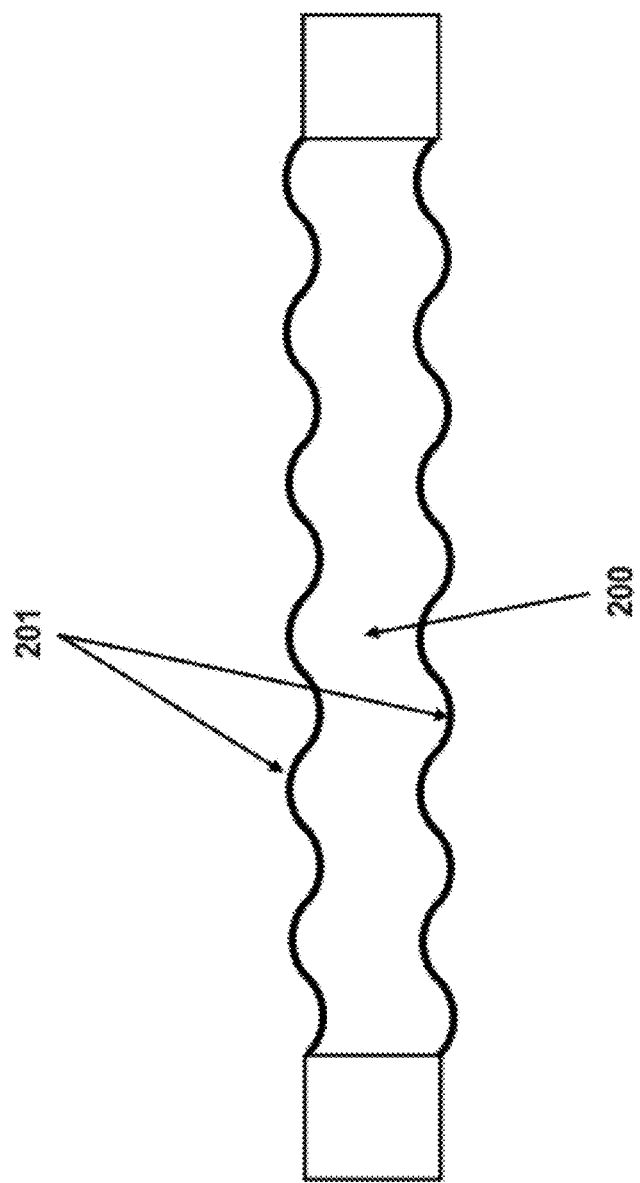

THREE-DIMENSIONAL FOCUSED ANTI-SCATTER GRID AND METHOD FOR MANUFACTURING THEREOF

This application claims the benefit of priority pursuant to 35 U.S.C. 119(e) from a U.S. provisional patent application having Application No. 61/391,536 filed Oct. 8, 2010.

FIELD OF THE INVENTION

The present invention generally relates to grids used in radiation imaging including x-ray imaging.

BACKGROUND OF THE INVENTION

The fields of medical and industrial radiography use the technique of directing beams of electromagnetic radiation toward an object (or part of the human body), so that the radiation passes through the object, to obtain an image of the interior of the Object, that is otherwise difficult to access or view directly without cutting through the body or other object. Usually, the electromagnetic radiations used for imaging purposes are x-rays, which tend to scatter as they travel through the object to be imaged.

The scattered x-rays contribute to the degradation of the image of the object and more particularly to the degradation of the image contrast. The x-rays that travel through the object that are not scattered are referred to as primary transmissions and it is those transmissions that contribute the most useful information to the image. The various unscattered x-rays passing though the object are attenuated at differing levels by differing amounts and compositions of material within the object. The differences in x-ray attenuation along linear paths through the object produce an intensity pattern that comprises image information which is recorded by an image receptor.

The image receptor may be a screen having a layer of x-ray sensitive material or x-ray sensitive electronic medium. The resulting image produced by the image receptor is based on the differences in the intensity of primary x-ray transmissions detected by the receptor. To improve the image quality, the primary x-ray transmissions and any scattered x-rays that would reach the image receptor after having traveled though the body, are first passed through a grid before they are allowed to impinge onto the image receptor.

It is understood that, quantitatively speaking, the scattered x-rays degrade the image contrast by a factor approximately equal to (1−SF) where SF is the scatter fraction of the total radiation transmitted through the body. The scatter fraction SF is defined as:

$$SF = \frac{S}{S+P}$$

where S and P are the intensities of the scattered and primary radiations incident on the image receptor, respectively.

SUMMARY OF THE INVENTION

The present invention provides a device for, and method of manufacture of, a focused anti-scatter grid for improving the image contrast of x-ray images produced in medical, veterinary or industrial applications.

In use, the grid is arranged to absorb as much of the scattered x-ray's as possible, and to transmit as much of the primary x-rays as possible, thus reducing degradation of the image contrast. The performance of the grid in this respect is given by the Contrast Improvement Factor (CIF):

$$CIF = \frac{C_g}{C_o} = \frac{1-SF}{1-\frac{S \times T_s}{S \times T_s + P \times T_p}}$$

where $C_g$ and $C_o$ are the image contrasts with and without the grid, $T_s$ and $T_p$ are the transmissions of scatter and primary radiation by the grid, respectively. By design considerations, improvement in contrast can be accomplished by increasing $T_p$ and by decreasing $T_s$. The design of the present invention is intended to reduce $T_s$ and, in many cases, will also increase $T_p$.

In accordance with the present invention the grid comprises a plurality of channels that are substantially transparent to x-rays and higher energy level radiation, and a series of walls formed of a material that is capable of absorbing such high energy radiation, the walls being so placed and aligned as to define the channels in such a manner as to focus any radiation passing through the channels on a single remote line or point. The walls absorbing any scattered radiation entering the grid with the focused radiation but which travel transversely to the focused radiation. The radiation absorbent walls are preferably supported by a frame, generally rectangular in outline. In one preferred embodiment, the frame, and the grid contained within the frame form a segment of a sphere, i.e. a portion of a spherical surface. The side of the grid facing the x-ray source and the object being imaged would have a radius of R, and the opposite surface a radius of R plus L, i.e., the height of the walls. To enhance the amount of T reaching the receptor, the grid can be effectively lengthened by corrugating the walls.

Another preferred embodiment of the focused grid of the present invention comprises an enclosed frame, comprising at least a pair of opposed side pieces, each supporting and positioning a ribbon of the material forming the grid walls. For example, each side piece is provided with a plurality of slots, or other openings, so spaced and disposed as to hold, preferably at each end, the material forming the walls defining the channels, in the proper alignment. The slots are so disposed relative to each other as to cause the wall materials held in the slots, to be in a configuration to focus any radiation impinging on one face of the grid to converge at a focus point, or line, beyond the opposing surface of the grid.

Preferably, the grid is formed of a series of interconnected and mating modules, each module being substantially identical to the other modules. In one such embodiment, each module is essentially a ribbon, or plate, of the radiation absorbent heavy metal material, held in a frame so as to maintain their juxtaposition relative to each other and to the radiation source and the imaging device. In another such embodiment, the ribbon, or plate, of the radiation absorbent heavy metal material is secured to one side of a suitably shaped support formed of a radiation transparent material, also preferably held in a suitable frame, as above.

In each preferred embodiment there is extending between, and defined by, the radiation absorbent walls, a substantially radiation transparent material, which most preferably is only, or primarily, air, the material most transparent to x-rays. Alternatively, as a means of providing additional structural support and rigidity to the radiation absorbent walls, extending between and attached to at least one of the immediately adjacent pair of defining walls is a solid support material that is also substantially transparent to x-radiation, such as a hydrocarbon polymer or carboxylated hydrocarbon polymer; if the polymer is thick enough to completely fill the channel between the walls, the polymer is more preferably foamed to further increase radiation transmission. The grid design most preferably contains primarily air within the channels, so that transmission of primary radiation ($T_p$) through the grid is maximized, thus allowing the radiation dose to the patient to be lower, as compared to conventional aluminum- or steel-supported grids.

The thickness of the heavy metal, x-ray absorbent walls defining the channels and the depth of the channels (and thus the length, L, of the walls) can be varied to optimize primary transmission and reduce or eliminate transmission of the scattered radiation, for a given radiation energy.

One preferred method of the present invention comprises the steps of forming a preferred grid frame by forming the frame sides, by casting or molding, of for example, aluminum or steel or a high strength polymer. In the method of forming one preferred embodiment of the frame, high precision machining of the aluminum or steel or rigid polymer frame sides, produces a series of aligned slits on opposite sides of the frame. The planes containing the center lines of the pairs of opposed slits along the opposing frame sides, are so aligned and juxtaposed, as to converge at a line on the horizontal plane of the x-ray tube focus, as depicted in FIG. 1.

The slits on opposite sides of the frame are precisely aligned so that slits on opposite sides are in the same planes orthogonal to the sides of the frame in which the slots are formed. The walls can be formed of thin ribbons of heavy metal foils held tightly in tension across the frame by the opposed slits. One embodiment is essentially a conventional linear grid where the metal foil ribbons form planes that extend from one edge of the frame to the other. In this embodiment the planes of all ribbons converge to a line through the x-ray focus. A second related embodiment is based upon the first embodiment, except that a second similar frame is positioned over the first but with the slits and ribbons orthogonal to those of the first layer. This design results in what is effectively a crossed linear grid, which further reduces scatter radiation striking the imaging surface and results in a further improved image. The grid ratio is the ratio of channel depth to diameter, which can be 3:1 to 20:1, and is preferably between 5:1 and 16:1.

Another embodiment of the present invention provides an improved, focused, antiscatter grid which comprises a plurality of substantially identical arc-shaped, mating modules, preferably comprising alternating layers of radiation transparent solid support material and radiation absorbent material. Preferably, each module is constructed from substantially radiation transparent solid material, such as a hydrocarbon polymer, and has at least one mating surface formed of a relatively thinner layer of radiation absorbent material. The modules are assembled to form a grid, preferably a plurality of focused channels, each bounded by radiation absorbent material; all of such channels are focused to the same point in space, intended to be located a certain distance from the assembled modules. The assembled modules are preferably mounted onto an appropriately shaped frame to form the focused grid of the present invention. In one preferred embodiment, the modules are corrugated, which corrugations are formed in a plane orthogonal to the direction of the focused radiation, and serve to extend the effective length of the grid, within a relatively compact frame allowing more primary radiation to pass to the receptor.

In a third embodiment, the focused grid of the present invention comprises a plurality of substantially identical arc-shaped, mating modules, preferably comprising alternating layers of radiation transparent solid support material and radiation absorbent material. Preferably, each module is constructed in the shape of a segment of a sphere, and may also be transversely corrugated in a continuous wave or sawtooth form. The modules are assembled to form a grid having a plurality of substantially x-radiation transparent focused channels, each defined by the layer of radiation absorbent material; all of such channels are focused as before. The assembled modules are preferably mounted onto an appropriately shaped frame to form the focused grid of this embodiment of the present invention.

BRIEF DESCRIPTION OF THE SEVERAL VIEWS OF THE DRAWING

FIG. 1 shows a generalized side view representation of the focused grid of the present invention placed between an object to be imaged and an image receptor.

FIG. 2 shows a side view representation of a preferred example of the focused grid of the present invention and its juxtaposition with respect to an x-ray source.

FIG. 2A shows an exploded view of a portion of the frame of the focused grid of the present invention in FIG. 2.

FIG. 3A shows a side view of a ribbon of a heavy metal foil, which forms a wall in the grid of FIGS. 2 and 2A.

FIG. 3B shows a side view of the ribbon of a heavy metal foil of FIG. 3A, where the ends of the foil have been folded into loops.

FIG. 3C shows a top view (from the direction of the x-ray source) of the ribbon of a heavy metal foil of FIG. 3B.

FIG. 9 shows side view of the tape-encased ribbon of FIG. 8; and

FIG. 9A shows a top view (from the direction of the x-ray source) of the ribbon of a heavy metal foil of FIG. 9, where the ends are held in the frame slits by crimped metal loops holding the ends of the ribbon.

FIG. 10 shows one spring tension system for adjusting the tension on the ribbons.

FIG. 11 shows a representation of the focused grid of the present invention placed between an object to be imaged and an image receptor.

FIG. 12 shows a perspective view of another preferred example of the spherical segment of the focused grid of the present invention.

FIG. 13 shows an exploded view of FIG. 12.

FIG. 14 shows a perspective view of one of the modules of the preferred example of the spherical segment shown in FIGS. 12 and 13.

FIG. 14A shows a perspective view of another embodiment of one of the modules of the preferred example of the spherical segment shown in FIGS. 12 and 13.

FIG. 14B shows a perspective view of another embodiment of one of the modules of the preferred example of the spherical segment shown in FIGS. 12 and 13.

FIG. 14C shows an end view of the embodiment of FIG. 14A

DETAILED DESCRIPTION OF THE INVENTION

Figure 4A:
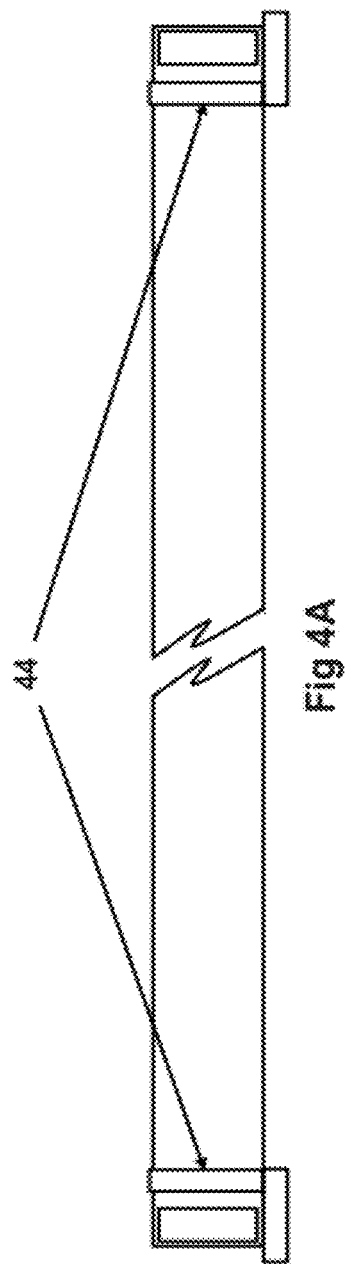
FIG. 4A shows a side view of the frame represented in FIG. 4 holding a ribbon of a heavy metal foil of FIG. 3B, the ribbon being held within the slits shown in FIG. 2A.

A preferred embodiment of the present invention provides an air-interspaced, focused grid, where the scatter-radiation absorbing walls of the channels are formed as a single layer of heavy metal foil which is held tightly in a frame on opposite margins of the supporting frame. The ribbon walls are held by the frame so as to be aligned to converge to a line in the plane of the x-ray source that is parallel to the plane of the anti-scatter grid. In the preferred embodiment, the frame is substantially rigid and capable of holding the plurality of tapes or foil ribbons in correct alignment in slits that are so aligned and juxtaposed as to support the foil tape or ribbon.

The focused grid of the present invention as described above can be used as an anti-scatter grid for x-ray imaging useful, for example, in the fields of medical and/or industrial radiography. Referring to FIG. 1, the x-rays are directed from the source (10) to pass through the object 12, to the image receptor 14, below, in passing through the object or patient, some of the x-rays are scattered 20, thus reducing the contrast in the recorded image. The grid of the present invention (16) is placed between the object or patient (17) and the image receptor (14). The grid is designed to absorb as much of the scatter radiation as possible while allowing the passage of the primary imaging x-rays.

The x-rays used for radiographic purposes usually include electromagnetic radiation having photon energies in the range of 10 keV to 1 MeV. For ease of explanation, the beam of radiation will henceforth be described as an x-ray beam in the range described. However, it should be understood that all of the embodiments of the claimed focused grid of the present invention may be operated and function as described using electromagnetic radiation having photon energies that fall outside of the range described above, with the boundaries or walls of the channels to be constructed from material that can absorb such scattered electromagnetic radiation as may be generated.

Continuing with the description of FIG. 1, a uniform beam 18 of x-rays is directed toward a surface of the object 12 and travels through the object 12 emerging from an opposite surface of the object 12. Differences in x-ray attenuation along linear paths through the object 12 produce an x-ray intensity pattern that comprises image information recorded by the image receptor 14. The image receptor 14 can be a device such as an intensifying screen coupled with a photographic film or any layer of x-ray sensitive material or x-ray sensitive electronic medium, which through one or more steps converts the x-ray intensity pattern into a visible image or visible format.

When x-rays 18 pass through the object 12, they are attenuated by a combination of scattering and absorption. X-rays which have passed through the object 12 and are "focused x-rays" (meaning they also pass through the grid 16, following a focused path as described herein) and are also referred to as 'primary x-rays'; the primary x-rays contribute to the formation of the image. That is, unscattered focused beams—having passed directly though the object 12—will mostly pass through the channels of the focused grid 16 of the present invention, Radiation, including x-ray radiation, which do not follow a focused path leaving the object being imaged are referred to as scattered, and scattered radiation 20 will intersect one of the metallic layers (or radiation absorbing layers) that define the channel boundaries, which are intended to absorb the scatter radiation to an extent depending on the composition and thickness of the boundary and the energy of the radiation. It must be noted that some focused x-rays, which pass in the plane of the foils will tend to be absorbed by those foils creating a shadow image of the foils in the resulting image. It is known to provide grid systems with a mechanism to move the grid during the x-ray exposure so that the image of the foils is reduced, if not eliminated, by the blurring resulting from the motion, without significantly reducing the resolution of the primary image.

The radiation absorbent channel boundary can be designed to a desired or preferable state by changing the constituent elements, i.e., different atomic numbers of its elements, or the thickness or density of the absorbent layer, to better suit the absorption of x-rays of a specific range of photon energies. For example in an application using low energy x-rays such as in mammography, the absorbent layer may be only a few tens of microns thick and might include elements with atomic numbers as low as 29. Applications requiring more energetic x-rays, such as general medical radiography, may employ a thicker absorbent layer, which is preferably formed from heavy metal elements with atomic numbers above 65, such as Lead, Bismuth, Tungsten, or Tantalum.

An x-ray transparent material (such as air, or a hydrocarbon polymer or other low molecular weight polymer which may also contain nitrogen or oxygen atoms) is a material through which an x-ray beam travels where the measurable intensity of the beam immediately prior to passing into the material is substantially equal to the measurable intensity of the beam immediately after exiting the material. Conversely, an x-ray absorbent material greatly reduces the amount of x-rays exiting such material compared to the strength of the x-ray's that entered such material. X-rays passing through the object being imaged, and that are scattered, i.e., that do not follow a focused path through the channels of the focused grid, intersect and impinge upon the x-ray absorbent wall boundaries of the focused channels, and are thus absorbed by these walls.

The ribbons of metal need not necessarily be pure metal but may be a powdered material mixed with binding agents (e.g., polymers) to bind a relatively high concentration of heavy metal in the form of a fine powder, or as a compound mainly containing elements with atomic numbers greater than 28, or as an alloy. Depending on the application for which the antiscatter grid is being used, the relatively high concentration of heavy metals may be in the range of 40% to 98% by weight. Because the channel boundaries are formed from foil under some degree of tension, some desirable, highly radiation-absorbent heavy metals, such as lead or bismuth or alloys thereof, will require reinforcement, such as by the addition of fibers or coatings (e.g., Mylar) to provide adequate tensile strength to a ribbon of the metal. This can include the use of glass fiber reinforced lead foil, or a lead foil wrapped in a thin braided weave of high tensile strength glass, nylon, polyester or other fiber materials. Alternatively, a thin tape may be adhered to the heavy metal ribbon formed, for example of Mylar or Kapton, two commercially available polymeric materials containing oxygen or nitrogen, respectively. As already described with respect to FIG. 1, the focused grid 16 of the present invention has a plurality of focused channels that allow unscattered primary x-ray beams having passed through the object 12 to impinge upon the image receptor 14, and thus form a clear, focused image.

Various portions of the ribbon embodiment of the focused grid of the present invention are depicted in different views, in FIGS. 2-10, to facilitate the description of the ribbon embodiment of the present invention. The drawings used in this application are not necessarily drawn to scale, but they are presented to clearly depict the various features and aspects of the present invention. Referring now to FIG. 2, the basic concept of the frame with slits to support, hold and align the metal foils, is shown. In FIG. 2, the slits 28 are formed along the margins of two opposing sides 24 of the open frame, are in planes that are aligned along straight line paths 26 to the x-ray source 22, and extend fully through the side of each side of the frame 24. A thin heavy metal foil ribbon 30 is stretched between a pair of the narrow slits 28 on opposite sides of the frame 24, so as to lie within the aligned plane extending between the slits.

Referring now to FIGS. 3A-C, the details of the foil ribbons are shown. The foils are made of suitable materials with adequate tensile strength and high atomic number such as tungsten, tantalum or alloys thereof, fabricated into foils of the desired thickness, and cut to ribbons of height 'd' and sufficient length 32 to traverse the distance between the opposite sides of the open frame, including the opposing slits FIG. 3A. Sufficient ribbon length is cut to permit the folding of ends into a loop with a triangular cross-section 34, shown in side view in FIG. 3B and in edge view in FIG. 3C. The purpose of the folds 34 at the ends of foil ribbons 30 is to prevent the ribbon from being pulled through the bracket slits 28 when under tension. The shape of the folds at the ends of the ribbons 30 is intended to maintain the foil precisely aligned with the centerline of the bracket slit and thus with the x-ray tube when the ribbon is held under tension.

Figure 4:
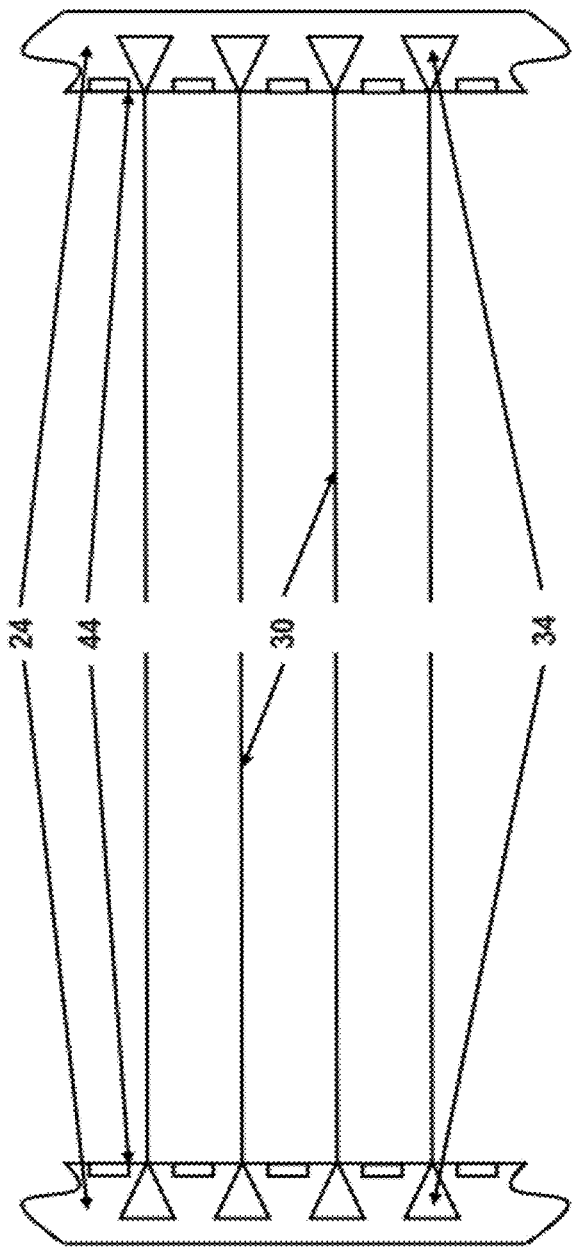
FIG. 4 shows a top view (from the direction of the x-ray source) of a portion of the frame represented in FIG. 2 holding a plurality of ribbons of a heavy metal foil of FIG. 3B, the ribbons being held within the slits shown in FIG. 2A.

Referring now to FIGS. 4 and 4A, the foil ribbon 30 with folded ends 34 is inserted into corresponding opposed slits in brackets 44 mounted on opposite sides of the frame 24. As can be seen, the folded loops at the ends are too large to fit through the slits 28, thus preventing the ribbon from slipping through the bracket when the frame is sized to produce tension on the ribbons. Referring to the preferred embodiment of FIG. 5, the foil ribbons are held between a fixed bracket 44 to the outer frame 24 while a second movable set of brackets 56 can be adjusted outward to pull the ribbons into tension across the frame, so as to insure they are aligned in the desired focusing plane.

In one embodiment the slits are present only on two sides of the grid frame (FIG. 6), creating narrow focused channels as in conventional linear grids. In this embodiment the foil ribbons 30 are tensioned between a fixed bracket 62 and an adjustable, movable bracket 56 on the opposite side of the frame. Referring back to FIG. 4 an important aspect of this design is that the shape of the folds 34 at the ends of the ribbons 30 ensures that when under tension each foil 30 is precisely aligned with the centerline of the bracket slit and thus with the x-ray source focus.

In this embodiment the scatter rejection capability would be similar to a conventionally fabricated linear grid with the same grid ratio, the same metal thickness and composition of channel walls, except that in accordance with this invention, the presence primarily of air in the channels between the metal ribbons ensures that the transmission of the primary radiation is substantially unimpeded and therefore superior.

Figure 7:
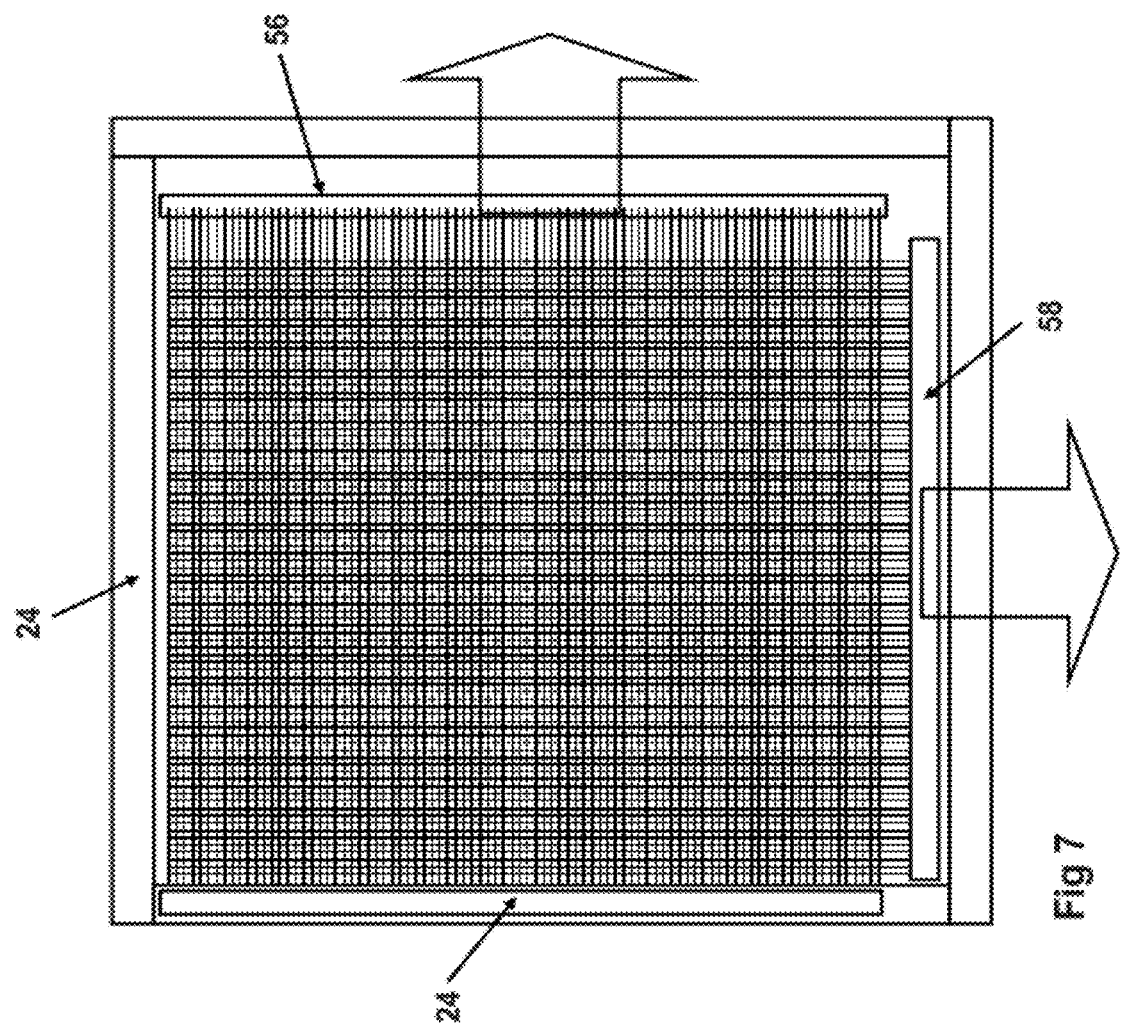
FIG. 7 shows a top view (from the direction of the x-ray source) of a pair of the complete adjustable frames represented in FIG. 6, juxtaposed orthogonally to each other to form a grid of squares.

In a second embodiment, shown in FIG. 7, there are two sets of opposing fixed brackets 24 and adjustable brackets 56, 58, one set positioned above the other in two layers, producing in effect a cross-hatched pattern. This embodiment would employ a single outer frame to which both sets of brackets are attached, so that the two sets of brackets are locked in orthogonal alignment with respect to the location of the x-ray focus. The advantage of this embodiment is that the scatter rejection would be considerably improved when compared to a conventional linear grid or that of the first embodiment, because scatter deflected into planes parallel to the grid ribbons in the first layer would be rejected by the transversely directed ribbons in the second layer.

In both embodiments the resulting grid is preferably covered on both top and bottom surfaces with thin Mylar polyester sheets to prevent entry of foreign materials, such as dust, into the open channel spaces, that might cause image shadows. Mylar film is substantially transparent to x-rays.

In another potentially less costly embodiment, the foil ribbons are made of lead or bismuth foil, possibly mixed in alloys also containing tin, antimony, indium or cadmium. In at least some of these cases, the resulting foil will not have sufficient tensile strength to be held in tension on the frame 24, and will require reinforcement with, e.g., a thin layer of Mylar or Kapton tape, such as on one or both surfaces of the foil. The films of Mylar or Kapton used for such tapes are usually about 1 mil in thickness. Alternatively a single steel reinforcing ribbon of the same thickness can be used.

Figure 8:
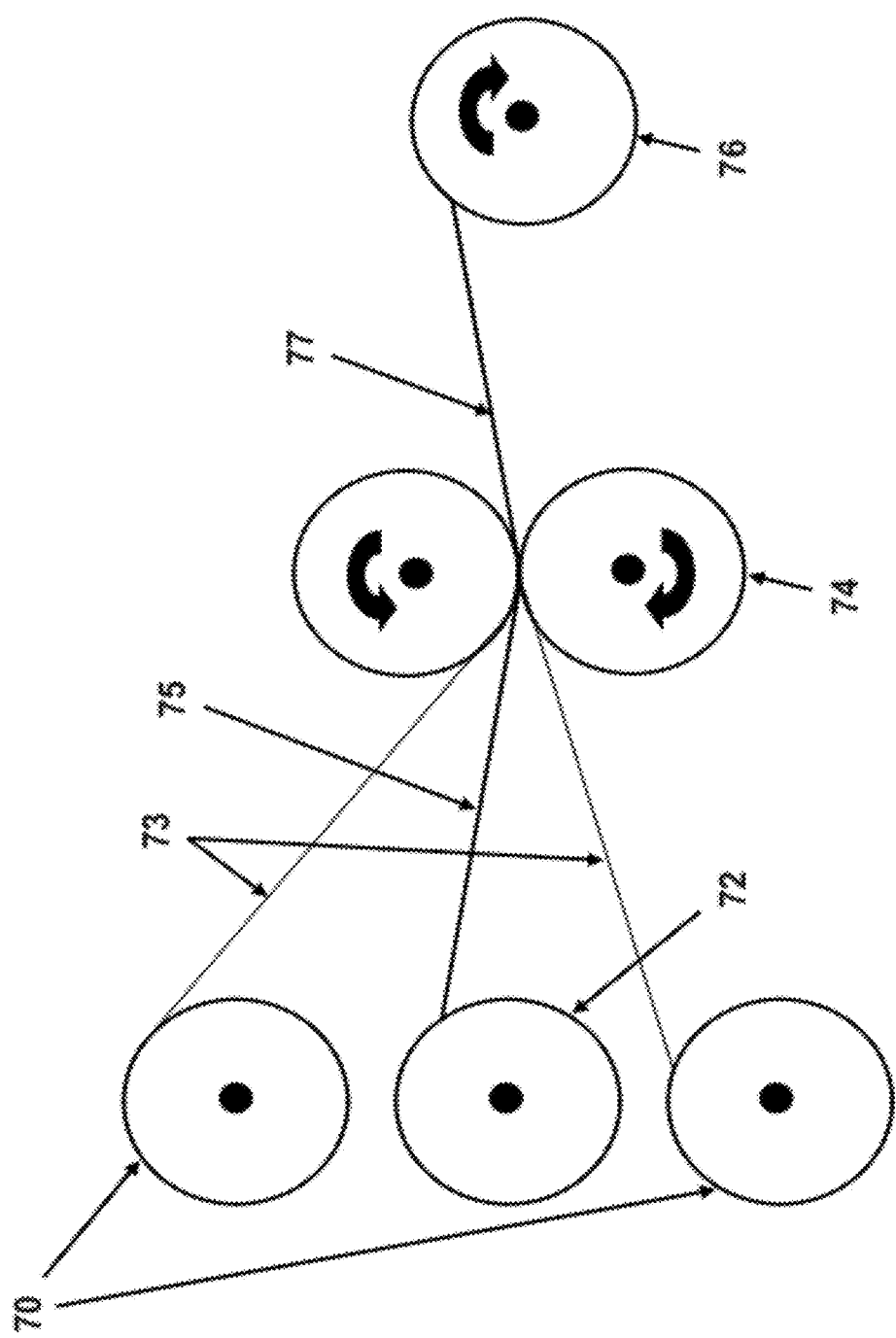
FIG. 8 shows a side representation of a system for forming a further improved embodiment of the ribbon forming the side walls of the grid, where the heavy metal ribbon is encased in a reinforcing tape.

A preferred process for assembly of this reinforced foil is shown in FIG. 8, where two rolls of Mylar or Kapton tape 70 are adhered to the opposite major surfaces of the lead, or other heavy metal foil or alloy foil 72, then fed through compression/gauging rollers 74 then onto a take-up reel 76. A similar process may be used with tapes constructed of polymer loaded metal powders of suitable heavy metals.

In the embodiment employing reinforced lead or alloy foils, it will not be possible to fold the ends of the ribbons creating a similar stop to fix the ribbon in position and to align it with the centerline of the bracket slit. Referring now to FIG. 9, the reinforced foil ribbons 80 are cut to precise lengths as required to traverse the frame but a steel, brass or other suitable metal clip is formed to a triangular shape in cross-section 82 and crimped over the ends of the reinforced ribbon. In this fashion, the crimped metal clip 82 forms a similar terminus on the reinforced foil ribbons so as to fix the position in the bracket slits and to align the foil to the slit margins.

In an example of this embodiment, a grid is prepared to reduce the scatter radiation for image receptors up to 43 cm×43 cm in size, where the x-ray source 10 focus to the image receptor 14 is a distance of 100 cm. The grid ribbons are constructed of tungsten foils 10 mm high ("L") and 100 microns in thickness, and cut to a length of 44 cm. A length of 4 mm at each end is folded to produce the triangular stop 34. Brackets 44 are produced with slits 28 cut by wire electrical discharge machining (wire EDM) or laser cutting, to provide a slit width of 150 microns. The slits 28 would be spaced along the brackets with an angular alignment between center planes of 0.0573 degrees with respect to the x-ray focus and a depth of 10.5 mm. The brackets can be constructed of angle steel beams with L-shaped cross-sections with a thickness of 3 mm and web diameters of 11 mm. The grid frame is constructed of mild steel alloy with an inner open area of 45 cm×45 cm with a thickness of 3 mm and a depth of 15 mm. The heavy metal ribbons preferably should be arranged so as to be separated by a distance of about 1 mm.

One embodiment of the tensioning mechanism for the adjustment of the movable frame bracket 56, as shown in FIG. 10, is provided preferably at both ends of the movable bracket 56. The tensioning mechanism is constructed using an m6 bolt 96, a coil spring 100 at each end of the adjustable ribbon bracket 56. The top and bottom surfaces of the grid frame would be covered with 25 micron Mylar sheets held in tension to prevent foreign material that might cause image artifacts from entering the space between ribbons.

In a further preferred example of this embodiment the outer grid frame of the first example is increased in depth to accommodate a second layer; The second layer contains a second set of brackets and ribbons essentially identical to that in the first layer, except that the slit separation angle would be increased to 0.0579 degrees with respect to the x-ray tube focus.

In yet another embodiment of the present invention there is provided a device and method of manufacture of an improved, focused, antiscatter grid. This embodiment of the focused grid of the present invention comprises a plurality of substantially identical arc-shaped, corrugated mating modules, preferably comprising alternating layers of substantially radiation-transparent solid support material and radiation-absorbent material. Preferably, each module is constructed from the radiation transparent support material coated with a relatively thinner layer of radiation absorbent material. The modules are assembled so that the support material and the absorbent material alternate to form a grid having a plurality of such focused channels, each bounded by radiation absorbent material; all of such channels are focused to the same point in space, intended to be located a certain distance from the assembled modules. The assembled modules are preferably mounted onto an appropriately shaped frame to form he focused arc-shaped grid of the present invention.

A further method of the present invention comprises the steps of forming, for example by injection molding, or by other thermoforming methods, a plurality of substantially identical mating modules made from substantially radiation transparent material, and applying a layer of radiation absorbent material to each of the mating modules. The modules are then mated into an assembly of a plurality of the modules to form focused channels; the assembly of focused channels is mounted onto a frame to form the focused grid of the present invention.

In one preferred embodiment of the present invention, there is provided a focused grid comprising a plurality of mating modules; each module having at least one mating side surface covered with a layer of radiation absorbent material and each module being constructed from radiation transparent material. The modules are assembled to form a grid having a plurality of focused channels for the passage of x-rays, each such channel containing the radiation transparent material and bounded by the radiation absorbent material; each such channel is focused to the same point in space, said point located a certain distance from the assembled modules. The assembled modules are mounted onto an appropriately shaped frame to form the focused grid of the present invention.

In one preferred embodiment, the shape of the focused grid is obtained from the projection of a square onto the surface of a sphere having a certain radius, R. The resulting structure is a spherical segment (i.e., a portion of a spherical surface) comprising a main inner surface having a radius R, a main outer surface, having a radius R', a first end and a second end. The spherical segment further has outer side surfaces.

The spherical segment is preferably formed from a plurality of substantially identical arc-shaped modules, constructed from radiation transparent material where each module has an outer radius, R'. Each module comprises opposing, mating side surfaces with mating structures, such as grooves (or corrugated surfaces), an arc-shaped top surface, an arc-shaped bottom surface, a first end and a second end. Further, preferably, for each arc-shaped module, at least one of the mating side surfaces (e.g., grooved or corrugated side surfaces) has a layer of a radiation absorbent material adhered thereto, such as a film or coating of a heavy metal.

An assembly of the arc-shaped modules has adjacently positioned arc-shaped modules mated to each other via their respective mating side surfaces, thus forming channels between the radiation-absorbent metal-coated side surfaces, permitting the guided passage of, e.g., x-ray radiation. The adjacently positioned modules may also be adhered to each other. Each such channel has a structure defined by the arrangement of radiation transparent material (i.e., the arc-shaped module) having one of its grooved side surfaces coated with a radiation absorbent layer (e.g., metal layer) and its opposing grooved side surface mated with or engaging a coated (with a radiation absorbent material such as a metal layer) grooved side surface of an adjacently positioned arc-shaped module, so that the radiation transparent material is bounded by radiation absorbent material (i.e., the metallic side surfaces).

Each of the channels has at least one focused axis, where each focused axis is defined by a path (preferably a linear path) originating from a point in space a certain distance from the inner surface of the grid, extending to a point on the inner surface of the spherical segment and through the radiation transparent material (e.g., an arc-shaped module) to a point on the outer surface of the spherical segment without having intersected any of the surfaces coated with a layer of radiation absorbent material that define the channel boundaries; such a path is called a "focused path", or "focused channel. The point in space that is located at the certain distance from the main inner surface of the spherical segment and from which the radiation emanates is herein defined as the "radiation source point". Preferably, the radiation source point is located a distance equal to R from the main inner surface of the spherical segment. R can be any real number greater than zero. It will be readily understood that the radiation source point may be located a distance other than R from the main inner surface of the spherical segment.

The assembly of the modules is mounted onto a suitably shaped frame having a structure that couples to or engages the first and second ends of the spherical segment and its outer side surfaces resulting in the focused grid of the present invention. The shape of the frame is also obtained from the projection of a square onto the surface of a sphere.

The assembled top surfaces of the arc-shaped modules form the main inner surface of the spherical segment and the assembled bottom surfaces of the arc-shaped modules form the main outer surface of the spherical segment. The first and second ends of the assembled arc-shaped modules form the first and second ends respectively of the spherical segment. The outer side surfaces of the outer arc-shaped modules of the assembled arc-shaped modules form the side surfaces of the spherical segment. It should be noted that the outer side surfaces of the spherical segment are preferably not corrugated, whereas the mating surfaces can and preferably are corrugated in some manner. The center of each arc-shaped module is the center of the spherical segment which is also the center of the sphere from which the spherical segment is created; said center is a point located in space a distance R away from any and all points on the main inner surface of the spherical segment; R is thus the radius of each of the arc-shaped modules and of the spherical segment.

Referring to FIG. 11, the focused grid 100 of the solid modular embodiment of the present invention is viewed from one of its ends showing the substantially trapezoidal shapes of the ends of the arc-shaped modules. It should also be noted that each of the cross sections of the modules viewed from one of their ends is also substantially trapezoidal in shape; the grid frame is not included in FIG. 1 for ease of explanation and illustration. The grid 100 is shown positioned intermediate an object 200 to be imaged (e.g., portion of a human body) and an image receptor 300 as shown. A radiation source tube 400 is positioned so that a radiation beam 500 originates from a radiation source point 300 for the focused grid 100 as shown.

Continuing with the description of FIG. 1, a uniform beam 500 of x-rays is directed toward a surface of the object 200 and travels through the object 200 emerging from an opposite surface of the object 200. Differences in x-ray attenuation along linear paths through the object 200 produce an x-ray intensity pattern that comprises image information recorded by the image receptor 300. The image receptor 300 can be a device such as an intensifying screen coupled with a photographic film or any layer of x-ray sensitive material or x-ray sensitive electronic medium, which through one or more steps converts the x-ray intensity pattern into a visible image or visible format.

The substantially x-ray-transparent solid materials, forming the main body of the arc-shaped modules of this embodiment, are created through an injection molding method—discussed infra—where the molded material is a rigid polymer composed mainly of relatively low atomic number elements, (e.g., Hydrogen and Carbon, and possibly Oxygen, and Nitrogen) and have a physical density preferably less than 1.2 g/cm$^3$ and are thus substantially transparent to x-rays. The x-ray transparency of these materials can be further enhanced by adding a foaming agent or micro bubbles to the polymer formulation during the molding process to further reduce the density, and thus increase the transparency of the final material.

The unscattered and focused beams may or may not have been attenuated when passing through the object being examined. X-rays which were scattered during the passage through the object being examined, do not follow a focused path through the channels of the focused grid, and thus intersect and impinge upon the x-ray absorbent boundaries of the focused channels and are thus absorbed by these layers. The absorbent layers are preferably formed of heavy metals such as Lead, Bismuth, Tungsten, or Tantalum. The layers of metal can also be made from low melting point alloys such as Low 117, Low 251 and Low 281, which are alloys of Bismuth with various combinations of Lead, Strontium, Cadmium and Indium. The layers of metal may not necessarily be pure metal, but may contain binding agents (e.g., polymers) to bind a relatively high concentration of heavy metal in the form of a fine powder or as a compound mainly containing elements with atomic numbers greater than 40. Depending on the application for which the antiscatter grid is being used, the relatively high concentration of heavy metals may be in the range of 40% to 98% by weight or volume of the absorbent layer.

As already described with respect to FIG. 11, the focused grid of the present invention has one or more focused channels that allow unscattered primary x-ray beams having passed through the object 200 to impinge upon the image receptor 300. An end view of the focused grid 100 is depicted showing the cross sections of each of the arc-shaped modules $100_1, \ldots, 100_M$ as being substantially trapezoidal in shape. As shown, there are M arc-shaped modules constituting the spherical segment, where M is an integer equal to 2 or greater.

Various portions of the focused grid of the present invention are depicted in different fashions in FIGS. 12-18 to facilitate the description of one embodiment of the present invention. The drawings used in this application are not necessarily drawn to scale, but they are presented to clearly depict the various features and aspects of the present invention.

A perspective view of the spherical segment of the focused grid of the present invention is shown in FIGS. 14 to 14C. FIGS. 14 A and B show individual arc-shaped modules 200 which can be assembled to form a spherical segment, as shown in FIG. 13, for example. Spherical segment 100A has a main inner surface and a main outer surface, generally designated b the numerals 106 and 108, respectively, formed by mating arc-shaped modules $100_1$ to $100_M$. Each of the arc-shaped modules $100_1$ to $100_M$ has respective first ends $112_1$ to $112_M$, respective second ends $114_1$ to $114_M$ and respective side surfaces $122_1, \ldots, 122_M$ and $120_1, \ldots, 120_M$. The spherical segment has outer side surfaces $122_1$ and $120_M$ (partially shown). The spherical segment 100 comprises M substantially identical arc-shaped modules assembled so that adjacently positioned modules mate or engage each along their side surfaces. In a preferred example, the sides are corrugated side surfaces, having different shapes for the corrugations. The spherical segment of the present invention when cut across line C—C is shown in FIG. 11, where the cross section of each of the arc-shaped modules is substantially trapezoidal shape.

Referring now to FIG. 13, a partially exploded depiction of FIG. 12 is shown whereby each of the arc-shaped modules $100_1, 100_2, 100_3$ to $100_M$ engages another adjacently positioned arc-shaped module along its corrugated side surface. The corrugations (which may be V-shaped grooves, as shown) for each of the modules are formed so that the assembly of arc-shaped modules (i.e., spherical segment 100 of FIG. 2) has aligned first and second ends as shown. As shown the peak of one corrugation fits into the groove of another. It should be noted that the dimensions of the corrugations relative to the dimensions of the arc-shaped modules are not necessarily drawn to scale. The arc-shaped modules have respective first ends $112_1, 112_2, 112_3$, to $112_M$, second ends $114_1, 114_2, 114_3$ to $114_M$, top surfaces $106_1, 106_2, 106_3$, to $106_M$, opposite side surfaces $122_1, \ldots, 122_M$ and $120_1, \ldots, 120_M$ and bottom surfaces $108_1, \ldots, 108_M$. Note the assembled top surfaces of the modules form main inner surface 106 and the assembled bottom surfaces form main outer surface 108.

Referring now to FIGS. 14-14C, there are shown perspective views of different arc-shaped modules $100_2$ for the grid of the present invention. It will be readily understood that for the embodiment of the invention discussed with respect to FIGS. 12-14, the arc shape modules $100_1 \ldots, 100_M$ in any one grid are substantially identical to each other. Thus all of the geometrical, physical and/or chemical features attributed to or described with respect to arc-shaped module $100_2$ apply to the remaining arc-shaped modules as well (i.e., modules $100_1$, $100_3 \ldots, 100_M$). Arc-shaped module $100_2$ has a top surface $106_2$ and bottom surface $108_2$ (not shown) similar in shape to top surface $106_2$ but convex rather than concave. Most preferably, the top and bottom surfaces are concentric. Each arc-shaped module, e.g., $100_2$, has a first end $112_2$ having front surface $112_2$A, side surfaces $112_2$B and $112_2$C, top surface $112_2$E and bottom surface $112_2$D, a second end $114_2$ having front surface $114_2$A, opposing side surfaces $114_2$B and $114_2$C, top surface $114_2$E and bottom surface $114_2$D. Side surface $122_2$ is structured in a similar manner to side surface $120_2$ (not shown) having corrugations which may be V-shaped grooves, or corrugations of other smoother curves, as shown. The depth of the focused grid of the present invention corresponds to the depth of each of the identical arc-shaped modules, which is shown as "L" for module $100_2$. In FIG. 14, the angled side segments of the grooves, or corrugations, form the surface of each arc-shaped module; the groove segments have dimensions "s," as shown, which are angled at 90° with respect to each other.

Still referring to FIG. 14, the width "w" is measured from a peak of one groove to a valley of another oppositely positioned groove as shown. The measurement "w" can be said to be the width of each of the focused channels of the grid. Side surface $122_2$ of module $100_2$ can be coated with a heavy metal (as discussed above) able to absorb radiation such as x-rays. One side surface $120_2$ can be left uncoated. Thus, corresponding side surfaces ($122_1$, $122_3$, . . . , $122_M$) of the other arc-shaped modules are similarly coated with a metallic layer and the corresponding opposite side surfaces ($120_1$, $120_3$, . . . , $120_M$) of the other arc-shaped modules are similarly left uncoated.

Referring back to FIGS. 12 and 13, arc-shaped module $100_2$ is shown mating with or engaging a side surface of arc-shaped module $100_1$ and also engages aside surface of arc-shaped module $100_3$ as shown in FIGS. 12 and 13. Referring now to FIGS. 12, 13 and 14, while side surface $120_2$ of arc-shaped module $100_2$ is not coated, the side surface $122_3$ (not shown) of the adjacent module $100_3$ with which side surface $120_2$ of arc shape module $100_2$ mates is coated and thus a channel is formed with the coated metal layer on side surface $122_2$ (i.e., a first boundary of the channel), arc-shaped module $100_2$ (i.e., a radiation transparent material) and a metal layer coated onto the facing side of adjacent arc-shaped module $100_3$ (a second boundary of the channel). Each of the focused channels is thus formed with an arc-shaped module bounded by one of its side surfaces coated with a metal layer and a metal layer coating on the adjacently positioned arc-shaped module.

Referring back to FIGS. 14 through 14C, when an arc-shaped module $100_2$ is assembled with the remaining M−1 arc-shaped modules, which must all have the same side surface contour, resulting in the spherical segment 100 as shown in FIG. 12, and said spherical segment 100 is positioned a distance R (shown in FIG. 14 as 118) from a radiation source point 300, where R is the radius of the spherical segment, the channels of the spherical segment are focused to the radiation source point 300. As already explained and it will be readily understood, that the distance 118 need not be equal to R, but can be any suitable distance allowing the focused grid of the present invention to operate or otherwise function as described herein, i.e., to exclude scattered x-rays.

An example of a focused axis is shown as path 116 originating from the radiation source point 300 and extending to top surface $106_2$ through arc-shaped module $100_2$ (made from x-ray transparent material) to outer surface $108_2$, where said path does not at all intersect or impinge upon the metallic layer boundaries, viz., side surface $122_2$ of arc-shaped module $100_2$ and the side surface $122_3$ (not shown) of adjacently positioned arc-shaped module $100_3$ that mates with side surface $120_2$ of arc-shaped module $100_2$. Thus, arc-shaped module $100_2$ forms a focused channel as defined herein where such channel has a channel depth of L and a channel width of w. The focused channel is bounded by x-ray absorbent layers $122_2$, bonded to the module $100_2$ and layer $122_3$ bounded to the module $100_3$.

Figure 15:
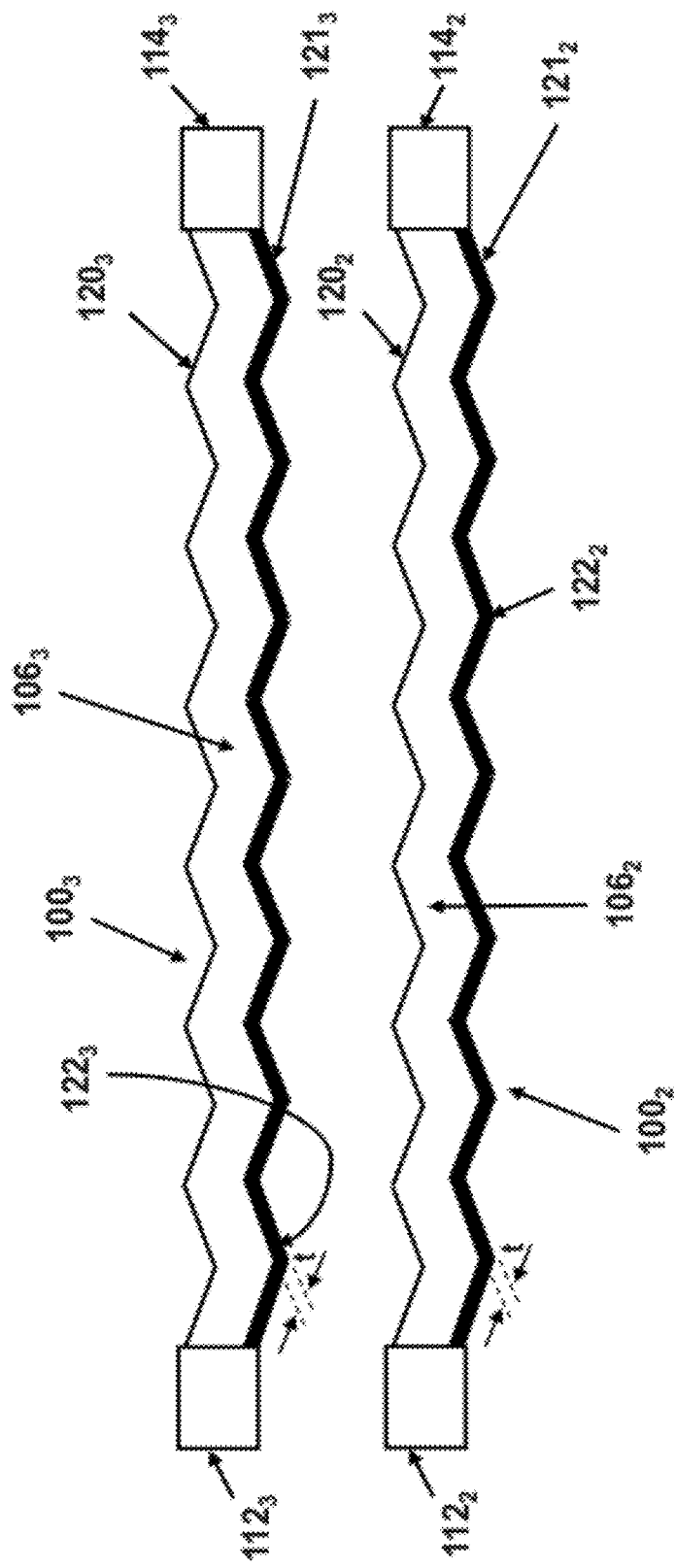
FIG. 15 shows a top view of two of the modules of the spherical segment of FIG. 12.

Referring now to FIG. 15, there is shown an exploded top view of a portion of FIG. 12, showing arc-shaped modules $100_2$ and $100_3$ positioned next to each other. Arc-shaped module $100_3$ has first end $112_3$, second end $114_3$, top surface $106_3$ and side surfaces $122_3$ and $120_3$. Arc-shaped module $100_2$ has first end $112_2$, second end $114_2$, top surface $106_2$ and side surfaces $122_2$ and $120_2$. A layer $121_3$ of metallic coating on side surface $122_3$ has a certain thickness t; for ease of illustration and description, the thickness of layer $121_3$ is drawn larger than if to scale relative to the width w (not shown in FIG. 15; see FIG. 14) of arc-shaped module $100_3$. Similarly, for arc-shaped module $100_2$ a layer $121_2$ of metallic coating on side surface $122_2$ has a certain thickness t; again for ease of illustration and description, the thickness of layer $121_2$ is not drawn to scale relative to the width w (not shown in FIG. 15; see FIG. 14) of arc-shaped module $100_2$.

Still referring to FIG. 15, one channel comprises metallic layer $121_2$, arc-shaped module $100_2$ and metallic layer $121_3$. In general, for the specific embodiment being discussed, each of the channels of the grid of the present invention comprises an x-ray transparent material positioned between two metallic layers, one of which is a layer on one side of the x-ray transparent material and the other metallic layer is a layer on an adjacently positioned mating arc-shaped module. All of the corresponding arc-shaped modules of the spherical segment 100 have respective layers $121_1$, . . . , $121_M$ of coated metal adhered to one of their side surfaces $122_1$, $122_2$, $123_3$, . . . , $123_M$.

Each of the respective opposite side surfaces $120_1$, $120_2$, $120_3$, . . . $120_{M-1}$ can be left uncoated, or may be coated if desired. Referring back to FIG. 12, it is clearly shown that arc-shaped module $100_M$ engages only one other module, viz., $100_{M-1}$, and thus to make an arc-shaped module function, as a focused channel, outer side $120_M$ is also coated with a metal layer.

Note that even though arc-shaped module $100_1$ also engages only one other module (i.e., module $100_2$), it functions as a focused channel because it is bounded by metal layers on side surfaces $122_1$ and $122_2$ (opposite side surface—not shown).

Figure 6:
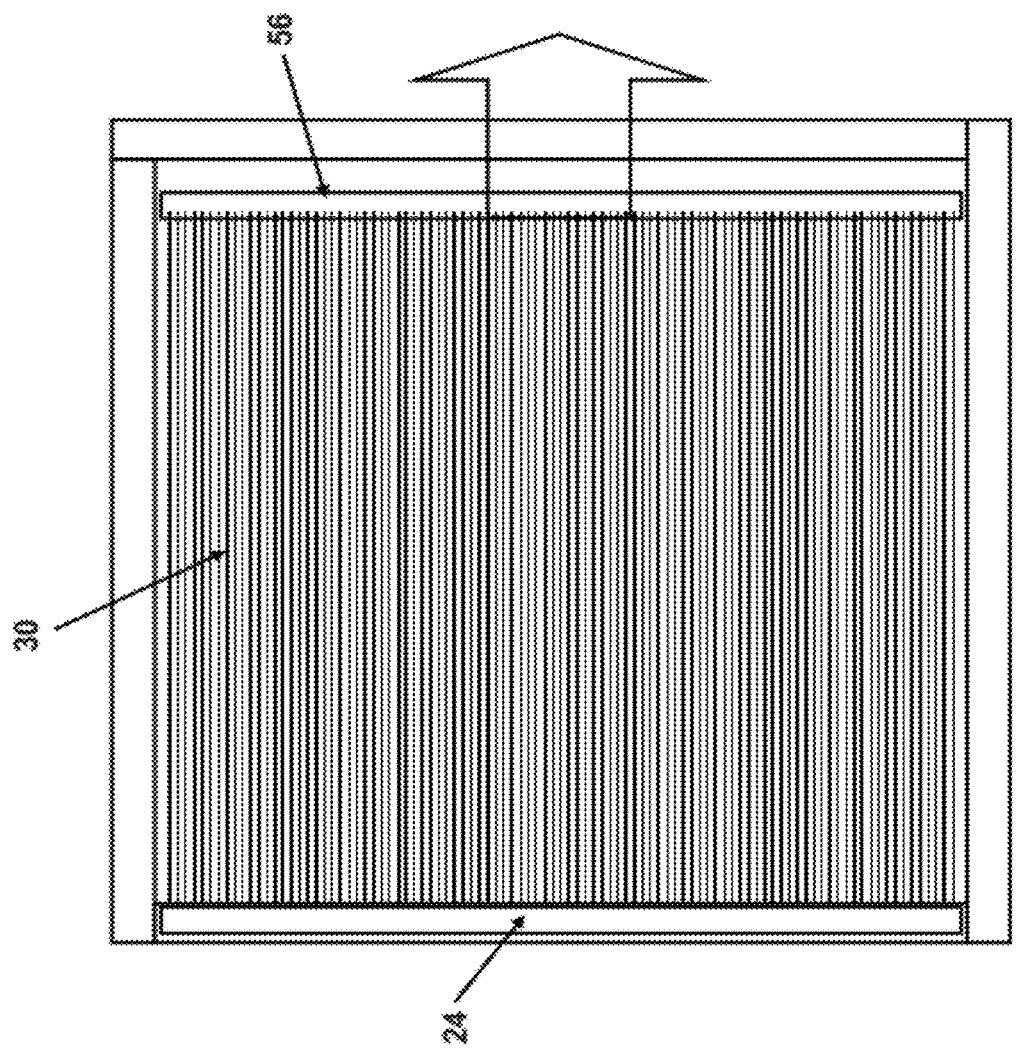
FIG. 6 shows a top view (from the direction of the x-ray source) of the complete adjustable frame represented in FIG. 5.
Figure 16:
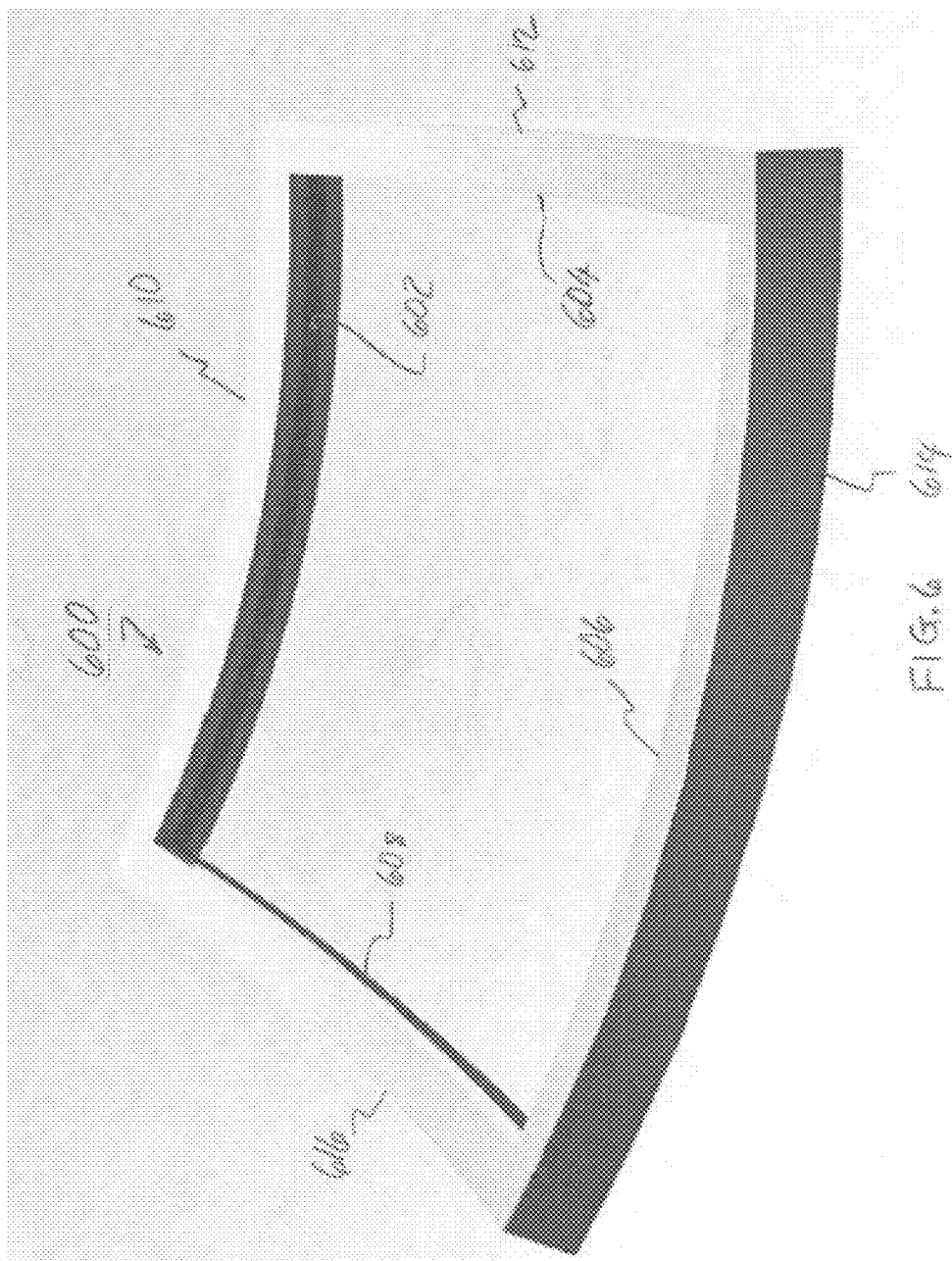
FIG. 16 shows a frame onto which the spherical segment of FIG. 12 can be mounted.
Figure 17:
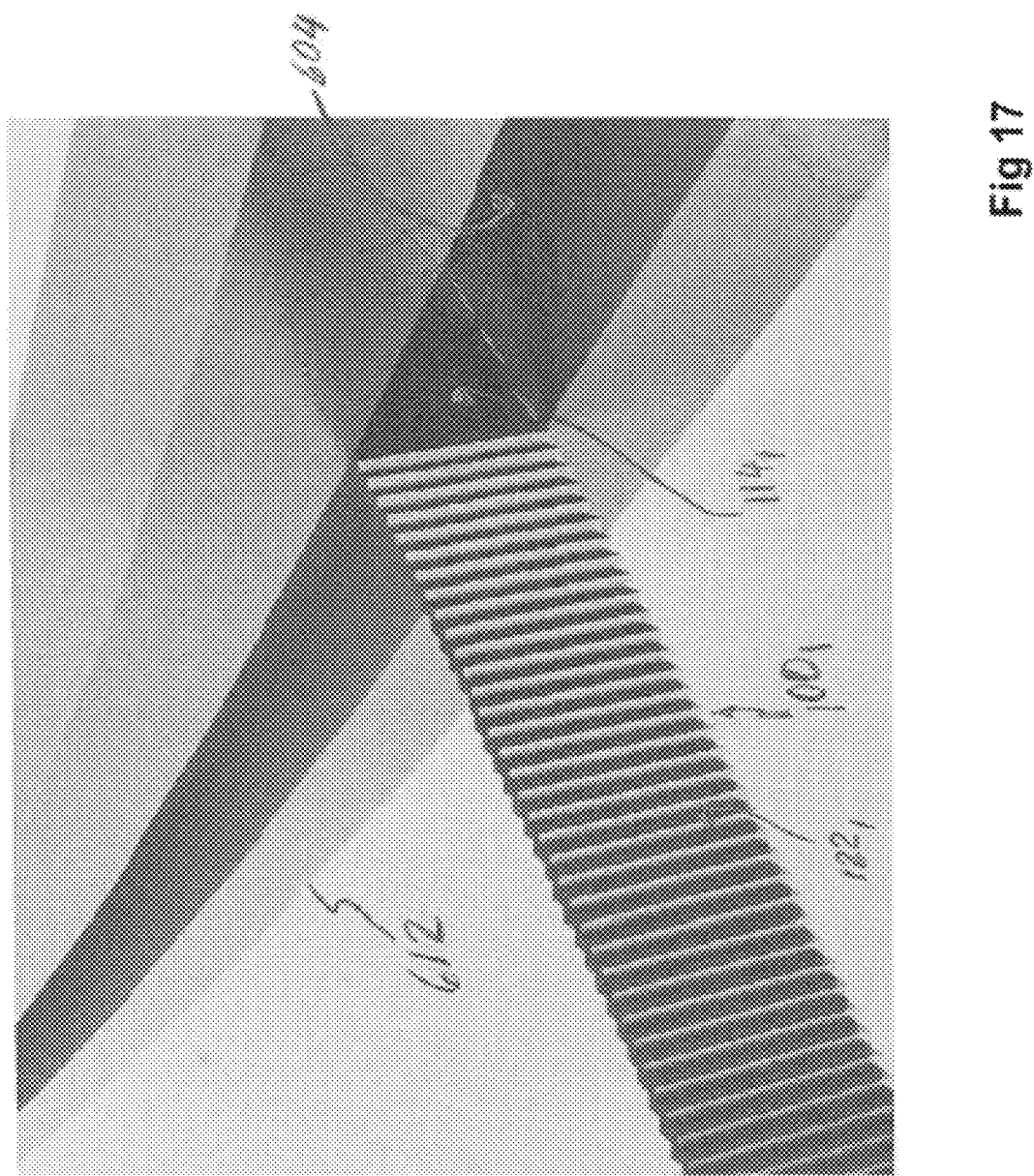
FIG. 17 shows a close up view of how a module of the spherical segment of FIG. 12 is coupled to the frame of FIG. 16.

Referring now to FIG. 16 there is shown frame 600 comprising sides 610, 612, 614 and 616 with respective inner slots 602, 604, 606 and 608. Only slot 602 is clearly shown in FIG. 6; oppositely positioned slot 606 is configured similarly to slot 602. Referring temporarily to FIGS. 6 and 2, oppositely positioned slots 602 and 606 are configured to receive outer surfaces $120_M$ and $122_1$ respectively of spherical segment 100. The ends 114 and 112 respectively of each of the M arc-shaped modules engage the slots 604 and 608 respectively of frame 600. That is, slot 608 (not shown) is configured to frictionally receive respective ends $112_1$, . . . , $112_M$ of the M arc-shaped modules. Similarly, and as shown in FIG. 7 for arc-shaped module $100_1$, slot 604 is configured to receive frictionally second ends $114_1$, . . . , $114_M$ of the M arc-shaped modules of spherical segment 100. The shape of the frame is also obtained by projecting a square onto the surface of a sphere having radius R.

For ease of explanation the spherical segment 100 as shown in FIGS. 12 and 13 and its portions shown in FIGS. 14 and 15 are oriented in the same manner so that the first ends $112_1, \ldots, 112_M$ face in the same direction. The focused grid of the present invention as shown in FIG. 11 (without frame 600) shows the front surfaces $112_1A, \ldots, 112_MA$ of the M arc-shaped modules.

Figure 18:
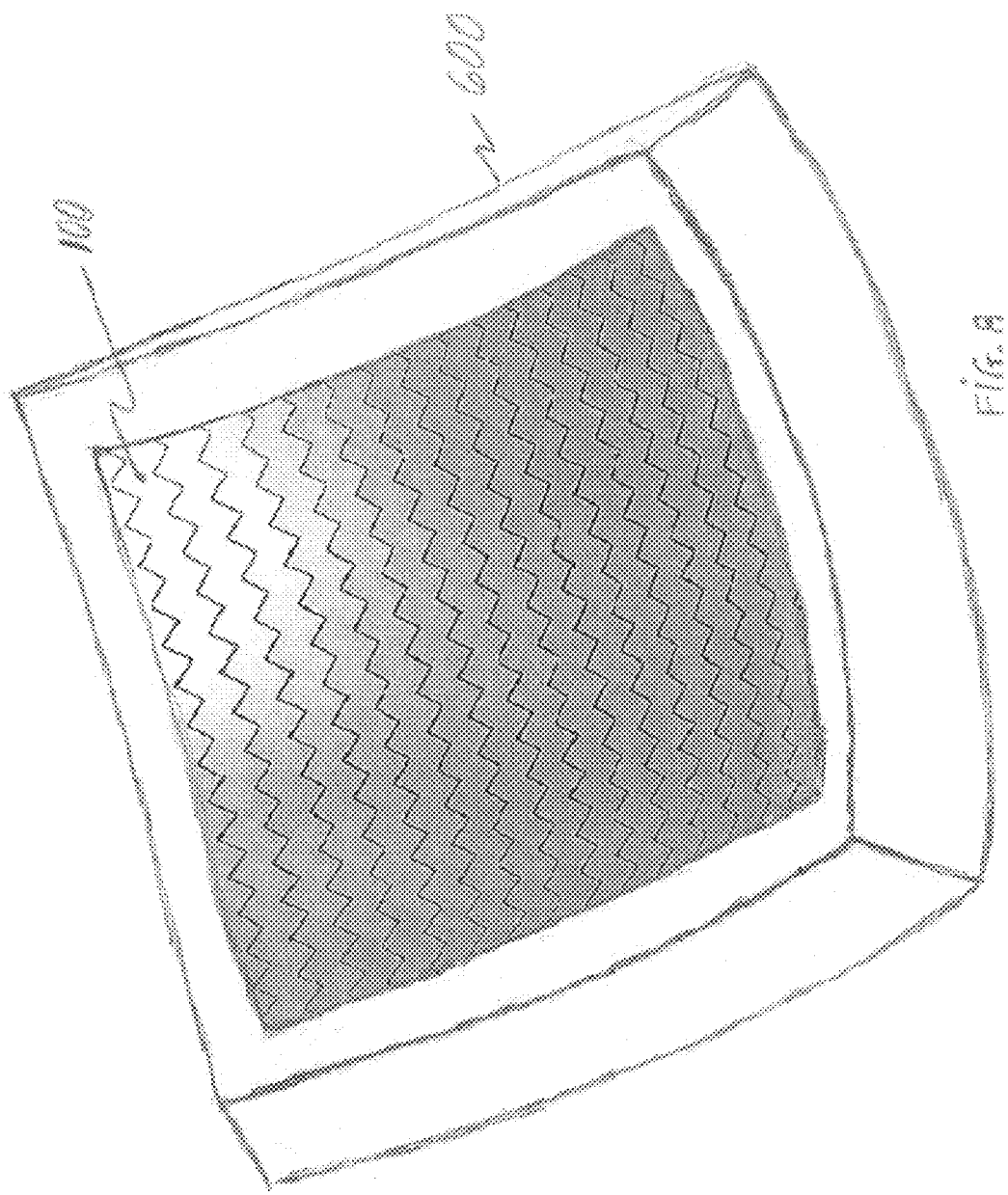
FIG. 18 shows one complete preferred embodiment of the focused grid of the present invention, where the preferred spherical segment of FIG. 12 is mounted onto the frame of FIG. 16.
Figure 19:
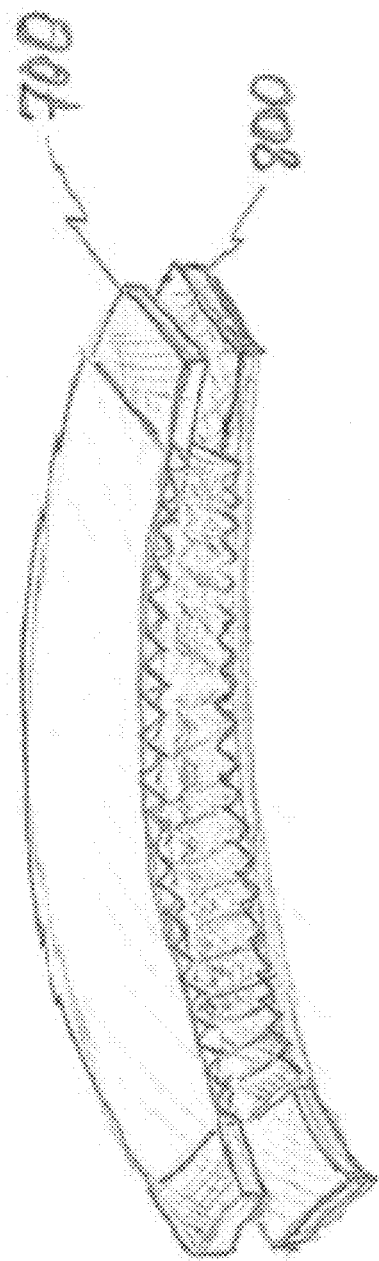
FIG. 19 shows examples of two forms that can be used in the process of injection molding to create the preferred arc-shaped modules.
Figure 20:
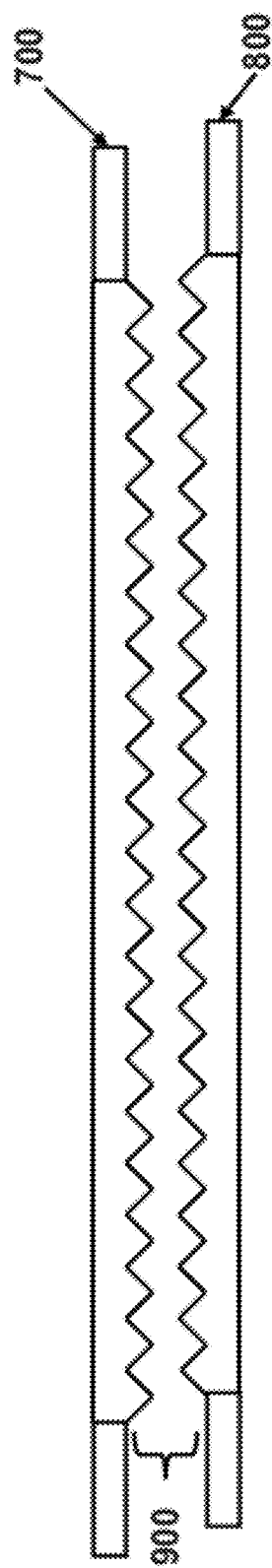
FIG. 20 is a front view of FIG. 19.

FIG. 18 shows a perspective view of the grid of the present invention as described herein including frame 600. One example of the manufacture of one of the embodiments of the focused grid of the present invention comprises the following steps. Each of the arc-shaped modules is produced using an injection molding method using a form consisting of a pair of plates 700 and 800 with grooved surfaces facing each other as shown in FIGS. 19 and 20. The facing plates are curved to the radius of the arc-shaped modules and said facing plates have V-shaped grooves on their facing surfaces as shown. The grooves contain groove segments of length "s" and said segments are angled at 90° with respect to each other. The resulting arc-shaped module will have a radius, R, equal to that of the facing plates.

For most medical radiography applications, the facing plates can be curved to have a radius of between 0.5 meters and 2.0 meters. The depth of the forms and thus of a resulting arc-shaped module (shown as L in FIG. 14) can be varied to obtain a desired performance. The plates are machined from aluminum or steel alloys commonly used to construct injection molds. The machining of the grooves employs computer controlled wire Electrical Discharge Machining (wire EDM) methods or other high resolution, high precision methods. The 90° grooves are machined into the surface of the curved plates so that lines along the grooves vertices and channels are convergent with the radiation source point when such point is located at distance, R, from the inner surface of the spherical segment 100.

In a first step, the facing plates are aligned to each other with the grooves of one plate aligned with the peaks of another and a gap is left between the aligned plates creating a form as shown in FIGS. 19 and 20. The gap 900 left between the plates is shown in FIG. 20.

Alternatively, the facing plates can be aligned such that the peaks on the surface of one plate align with the peaks of the surface of another plate forming diamond shaped gaps (not shown), instead of a corrugated shaped gap. In a second step, radiation transparent material (e.g., an x-ray transparent material such as a polymer material) is injected into the form, i.e., into the gap between the facing plates, and thus injection molds an arc-shaped mating module as shown in FIG. 14. As discussed previously the material injected into the form is x-ray transparent and such x-ray transparency can be enhanced by the addition of a foaming agent or micro bubbles to the material (e.g., a polymer formulation) during the molding process.

Examples of suitable rigid polymers include ABS polymers, polyacetals, polyacrlates, polyamides (nylon), polycarbonates, polyethylenes, polypropylenes, polystyrenes, rigid vinyl polymers, as well as melamines, polyesters, epoxies, and blended polymers such as ABS/Polycarbonate, ABS/PVC, and PVC/Acrylic polymers and copolymers such as styrene/butadiene copolymers. These polymers are mainly carbon and hydrogen atoms, with some other elements, such as oxygen or nitrogen.

In a third step, a radiation absorbent material, such as a metal coating made from any one of various metals and/or alloys discussed herein, is applied to one mating side surface (e.g., a grooved surface) of the module and is caused to adhere to the side surface; the metal coating layer has a thickness, t.

Any one of several methods for forming the layer is possible. For example, the layer can be formed through the use of electroplating the metal onto the module. Also casting or injection molding of a low melting point heavy metal alloy can be used to form the layer. Another method for forming the layer is the process of stamping, vacuum forming or pressure forming of a thin malleable metal layer onto a form or directly onto the radiation transparent material. Yet another layer forming method that can be used is a thermal spray process.

One example of a thermal spray process is a plasma spray process wherein plasma gas is heated by an arc formed by two electrodes. As the plasma gas is heated by the arc, it expands and is accelerated through a shaped nozzle, creating relatively high velocities of the heated plasma. The metallic material (or a mixture of the metallic material and one or more polymers in powder form or molten form) is injected into the high speed plasma. The material is rapidly heated and accelerated to a relatively high velocity and impacts the surface being coated and rapidly cools forming the coating.

In a fourth step a plurality (say M where M is an integer equal to 2 or greater) of the modules coated on one side with a metal layer are assembled. An adhesive can be used to adhere adjacently positioned arc-shaped mating modules to each other (see for example, FIG. 12) into an assembly and such assembly can be mounted onto a frame by sliding their ends onto receiving slots of the frame to frictionally attach to the frame and each such mounted module is caused to abut adjacently positioned modules. The assembly has outer modules with outer surfaces. The outer side surfaces of the outer modules of the assembly of modules (e.g., a spherical segment such as depicted in FIG. 2) can also frictionally fit into receiving slots of the frame.

An adhesive may be used to attach the outer surfaces of the assembled modules (i.e., outer side surfaces of the outer modules—first module, module $100_1$ with outer side surface $122_1$ and the last module—module $100_M$ with outer side surface $120_M$) to the frame 600. The outer side surfaces can also be attached to the frame with an adhesive and not necessarily be frictionally fit into a slot. Suitable adhesives depend upon the material forming the grid modules and the frame. Two-part and one-part epoxies are useful for a wide range of polymers, as are cyanoacrylates and polyurethane adhesives.

The resulting grid, as shown in FIG. 18, shows the spherical segment 100 of FIG. 2 mounted onto the frame 600 of FIG. 16.

Currently available grids are typically specified in terms of grid ratio, i.e., the ratio of channel depth to channel diameter or width. The same approach can be used for the focused grid of the present invention where the grid ratio is (L/W) (i.e., the ratio of channel depth, L, to channel width, W). A desirable set of dimensions for a grid—particularly a grid used generally for radiography purposes—is that the channel width, i.e., W, is approximately 1 mm. Thus, for a highly preferred range of grid ratios of 8:1 to 16:1, the channel depth will fall in the range of 8-16 mm.

Figure 5:
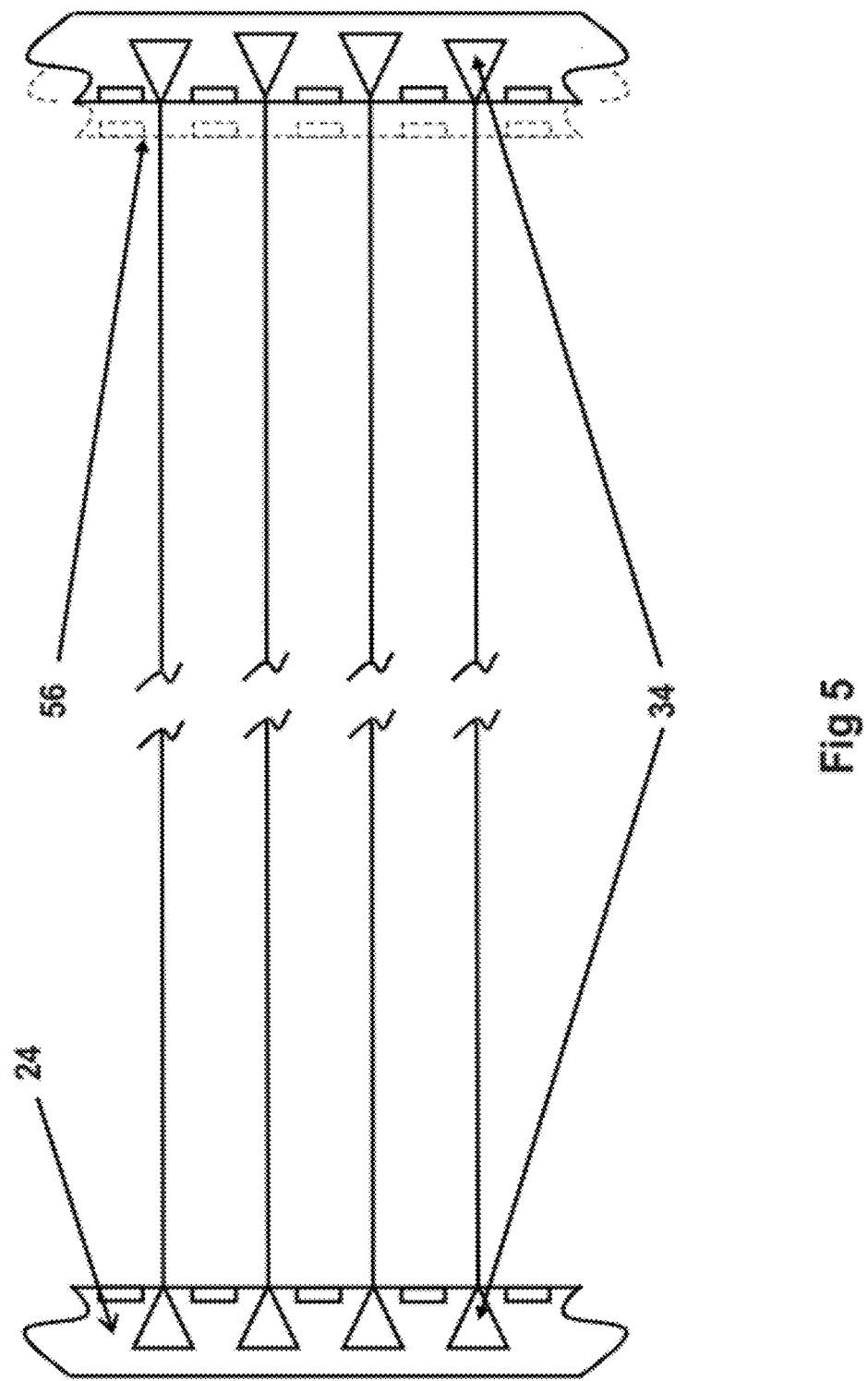
FIG. 5 shows a top view (from the direction of the x-ray source) of a portion of an adjustable frame represented in FIG. 4 holding a plurality of ribbons of a heavy metal foil of FIG. 3B, the ribbons being held within the slits shown in FIG. 2A.

An important performance characteristic of a grid is called the primary transmission P, which is defined by the following formula:

$$P = s/(s+t)e^{-\mu(E)L}$$

where t is the metal layer thickness as shown in FIG. 5, and it is assumed that $W = s\sqrt{2}$. The second term of the equation, viz., ($e_{-\mu EL}$), is an expression that reflects the attenuation of the x-rays as they pass through the focused grid of the present invention, where L is the depth of the focus grid and $\mu_E$ is a linear attenuation coefficient for x-ray photons, of energy E, in the x-ray transparent material from which the arc-shaped modules are made.

The primary transmission P represents the percentage of transmission that passes through the x-ray transparent material for a certain width, W, and depth, L, of the material and metal layer thickness, t. For a channel width, W, of 1.414 mm, the metal layer thickness would range from 0.0525 to 0.25 mm for primary transmissions, P, that range from 95% to 80% without the x-ray transparent material, respectively. For a channel made with a polymer material, the attenuation coefficient, $\mu_E$, will vary with x-ray energy and with polymer density, which desirably should be less than 1.2 g/cm3. Considering the geometry and attenuation of the polymer material, the total primary transmission at 50 keV will range between 61% and 72% depending on metal thickness, t, and the density of the polymer material.

Referring back to FIGS. 12-18, one particular grid designed and manufactured in accordance with the claimed focused grid of the present invention is a grid made from the arc-shaped modules of this invention, having a radius of R=985 mm, with L=13 mm, W=1.4 mm, t=0.1 mm and the grooves form 90° angles, and for the groove segments, s=1.0 mm; the arc-shaped modules are molded from ABS (Acrylonitrile Butidiene Styrene) polymer (specifically, a super high impact ABS plastic, such as TP1 Porene® Grade ABS-SP-100-BK, having a $\mu_E$=0.208 cm−1, at 50 keV, and plasma-coated with a layer of Bismuth metal. The final grid is installed in a frame having the dimensions 450 mm×450 mm, which contains 430 individual modules adhesively connected to each other. It is understood that it is possible to avoid the use of adhesives, and merely mechanically press the modules together within the frame.

Throughout this description supra, the values of variables, R, L, W, t, and s are real numbers greater than zero.

It will be readily understood that the overall shape of the focused grid of the present invention may be obtained from the projection of an N-sided polygon onto a geometrical surface having at least one or more foci. In the case of a sphere, discussed above, there is one focus which is the center of the sphere. It should be noted that a rectangle, a triangle or any well known N-sided polygon (where N is an integer equal to 3 or greater) can be projected onto the surface of a sphere or any other three dimensional surface (e.g., surface of a spheroid or ellipsoid) to obtain the shape of the focused grid. It will therefore be readily understood that the shape of the claimed focused grid of the present invention is not limited to a spherical segment.

The various aspects, characteristics and architecture of the device and method of the present invention have been described in terms of the embodiments described herein. It will be readily understood that the embodiments disclosed herein do not at all limit the scope of the present invention. One of ordinary skill in the art to which this invention belongs can, after having read the disclosure, may readily implement the device and method of the present invention using other implementations that are different from those disclosed herein but which are well within the scope of the claimed invention, as defined by the following claims.

The invention being claimed is as follows:

1. A focused grid comprising: a plurality of modules, each module comprising alternating radiation transparent materials and radiation-absorbent materials, the modules being formed of arc-shaped molded polymer material covered along at least one side surface with a heavy metal layer, the top and bottom surfaces of each module being arcuate in two orthogonal directions, the modules forming each grid being substantially identical to each other so that when a plurality of the modules are mated together, the mated modules form a spherical section, and focused channels for the passage of x-radiation are formed through the polymer material, between the heavy metal layers of adjacently positioned modules; and a frame onto which the plurality of module are mounted and secured in the desired juxtaposition.

2. The focused grid of claim 1 where each of the modules has a pair of side surfaces and at least one side surface has a contour adapted to mating with a side surface of another such module.

3. The focused grid of claim 2 where the at least one mating surface comprises a corrugated surface formed with V-shaped or undulating grooves.

4. The focused grid of claim 2 where the heavy metal is selected from the group consisting of lead, bismuth, tungsten and tantalum, and alloys thereof.

5. The focused grid of claim 4 where the heavy metal alloy is a low melting alloy combining Bismuth and Lead, Strontium, Cadmium and Indium.

6. The focused grid of claim 2 where the polymer material is a substantially rigid polymer composed mainly of the low atomic number elements Hydrogen, Carbon, Oxygen or Nitrogen, and having a density of less than 1.2 grams per cubic centimeter, so as to be substantially radiation-transparent.

7. The focused grid of claim 6 where the rigid polymer is selected from ABS, Urethane, acrylic or polycarbonate.

8. A method for manufacturing the focused grid of claim 1, the method comprising: forming a plurality of substantially identical arc-shaped, polymer radiation-transparent modules covered along at least one side surface with a strip of radiation-absorbent material of heavy metal, joining the plurality of heavy metal layer covered modules to each other so that when a plurality of the modules are mated together, the mated modules form a spherical section, each arc-shaped molded polymer module being separated from its adjacent such polymer module by a strip of radiation-absorbent material, so as to form the radiation transparent channels defined by the focusing heavy metal layers, and assembling, the joined modules in a frame such that adjacently positioned modules are so juxtaposed one with each other to form focused channels, thus forming the grid of alternating layers of radiation-transparent material and radiation-absorbent strips, such that adjacently positioned modules are so juxtaposed one with each other to form focused channels; the plurality of modules are so mounted and secured on the frame so as to maintain the desired spherical section.

9. The method for manufacturing the focused grid in accordance with claim 8, wherein the heavy metal strip is coated onto the polymer module.

* * * * *